(12) United States Patent
DiMarchi et al.

(10) Patent No.: US 9,018,164 B2
(45) Date of Patent: Apr. 28, 2015

(54) GLUCAGON ANALOGS EXHIBITING PHYSIOLOGICAL SOLUBILITY AND STABILITY

(75) Inventors: Richard D. DiMarchi, Carmel, IN (US); David L. Smiley, Bloomington, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 418 days.

(21) Appl. No.: 13/357,170

(22) Filed: Jan. 24, 2012

(65) Prior Publication Data

US 2012/0196804 A1    Aug. 2, 2012

Related U.S. Application Data

(63) Continuation of application No. 12/092,802, filed as application No. PCT/US2006/043334 on Nov. 6, 2006, now Pat. No. 8,338,368.

(60) Provisional application No. 60/734,307, filed on Nov. 7, 2005.

(51) Int. Cl.
*A61K 38/26* (2006.01)
*C07K 14/605* (2006.01)

(52) U.S. Cl.
CPC ............... *A61K 38/26* (2013.01); *C07K 14/605* (2013.01)

(58) Field of Classification Search
USPC ........................................................ 514/7.2
See application file for complete search history.

(56) References Cited

U.S. PATENT DOCUMENTS

| | | | |
|---|---|---|---|
| 4,275,152 A | 6/1981 | Esders et al. | |
| 5,359,030 A | 10/1994 | Ekwuribe | |
| 5,510,459 A | 4/1996 | Smith et al. | |
| 5,512,549 A | 4/1996 | Chen et al. | |
| 5,545,618 A | 8/1996 | Buckley et al. | |
| 5,665,705 A | 9/1997 | Merrifield et al. | |
| 5,783,674 A | 7/1998 | Geysin et al. | |
| 6,191,102 B1 | 2/2001 | DiMarchi et al. | |
| 6,583,111 B1 | 6/2003 | DiMarchi et al. | |
| 6,677,136 B2 | 1/2004 | Marshall et al. | |
| 7,192,922 B2 | 3/2007 | Shannon et al. | |
| 7,211,557 B2 | 5/2007 | DiMarchi et al. | |
| 7,314,859 B2 * | 1/2008 | Green et al. | 514/5.9 |
| 7,326,688 B2 | 2/2008 | O'Harte et al. | |
| 7,557,183 B2 | 7/2009 | DiMarchi et al. | |
| 7,576,059 B2 | 8/2009 | Jonassen et al. | |
| 8,053,560 B2 | 11/2011 | Sheffer et al. | |
| 2002/0049164 A1 | 4/2002 | Demuth et al. | |
| 2003/0021795 A1 | 1/2003 | Houston et al. | |
| 2003/0143183 A1 | 7/2003 | Knudsen et al. | |
| 2003/0195157 A1 | 10/2003 | Natarajan et al. | |
| 2003/0204063 A1 | 10/2003 | Gravel et al. | |
| 2004/0002468 A1 | 1/2004 | Wadsworth et al. | |
| 2004/0235710 A1 | 11/2004 | DeFilippis et al. | |
| 2005/0070469 A1 | 3/2005 | Bloom et al. | |
| 2005/0095679 A1 | 5/2005 | Prescott et al. | |
| 2005/0124550 A1 | 6/2005 | Peri | |
| 2005/0153890 A1 | 7/2005 | Pan et al. | |
| 2005/0288248 A1 | 12/2005 | Pan et al. | |
| 2006/0003417 A1 | 1/2006 | Pan et al. | |
| 2006/0003935 A1 | 1/2006 | Pan et al. | |
| 2006/0084604 A1 | 4/2006 | Kitaura et al. | |
| 2006/0160722 A1 * | 7/2006 | Green et al. | 514/3 |
| 2006/0171920 A1 | 8/2006 | Shechter et al. | |
| 2006/0210534 A1 | 9/2006 | Lee et al. | |
| 2006/0252916 A1 | 11/2006 | DiMarchi et al. | |
| 2006/0286129 A1 | 12/2006 | Sarubbi | |
| 2007/0042956 A1 | 2/2007 | Johansen et al. | |
| 2007/0173452 A1 | 7/2007 | DiMarchi et al. | |
| 2007/0203058 A1 | 8/2007 | Lau et al. | |
| 2007/0287670 A1 | 12/2007 | Natarajan et al. | |
| 2008/0113905 A1 | 5/2008 | DiMarchi et al. | |
| 2008/0125574 A1 | 5/2008 | Sheffer et al. | |
| 2008/0312157 A1 | 12/2008 | Levy et al. | |
| 2008/0318837 A1 | 12/2008 | Quay et al. | |
| 2009/0036364 A1 | 2/2009 | Levy et al. | |
| 2009/0054305 A1 | 2/2009 | Schlein et al. | |
| 2009/0062192 A1 | 3/2009 | Christensen et al. | |
| 2009/0074769 A1 | 3/2009 | Glaesner et al. | |
| 2009/0137456 A1 | 5/2009 | DiMarchi et al. | |
| 2009/0186817 A1 | 7/2009 | Ghosh et al. | |
| 2009/0192072 A1 | 7/2009 | Pillutla et al. | |
| 2010/0190699 A1 | 7/2010 | DiMarchi et al. | |
| 2010/0190701 A1 | 7/2010 | Day et al. | |
| 2010/0204105 A1 | 8/2010 | Riber et al. | |
| 2011/0065633 A1 | 3/2011 | DiMarchi et al. | |

(Continued)

FOREIGN PATENT DOCUMENTS

| | | |
|---|---|---|
| CA | 2024855 | 3/1992 |
| EP | 0220958 | 5/1987 |

(Continued)

OTHER PUBLICATIONS

"Novel Glucagon-Based Peptides—Virtues of Combinatorial Pharmacology," AAPS 2005, San Francisco, California.

Ahn, J.M. et al., Development of potent truncated glucagon antagonists, *J. Med. Chem.*, 44(9): 1372-9, Apr. 26, 2001. (Abstract).

Ahn, J.M. et al., A new approach to search for the bioactive conformation of glucagon: positional cyclization scanning, *J. Med. Chem.*, 44(19): 3109-16, Sep. 13, 2001.

Althage et al.,JBC "Targeted Ablation of GIP-Producing Cells in Transgenic mice reduces obesity and insulin resistance induced by a high fat diet" 2008).

(Continued)

*Primary Examiner* — Gyan Chandra
(74) *Attorney, Agent, or Firm* — Barnes & Thornburg LLP

(57) ABSTRACT

Modified glucagon peptides are disclosed having improved solubility and stability, wherein the native glucagon peptide has been modified by pegylation, or the addition of a carboxy terminal peptide selected from the group consisting of SEQ ID NO: 19, SEQ ID NO: 20, SEQ ID NO: 21, or both.

19 Claims, 2 Drawing Sheets

(56) References Cited

U.S. PATENT DOCUMENTS

| | | | |
|---|---|---|---|
| 2011/0098217 | A1 | 4/2011 | DiMarchi et al. |
| 2011/0166062 | A1 | 7/2011 | DiMarchi et al. |
| 2011/0190200 | A1 | 8/2011 | DiMarchi et al. |
| 2011/0257092 | A1 | 10/2011 | DiMarchi et al. |
| 2011/0288003 | A1 | 11/2011 | DiMarchi et al. |

FOREIGN PATENT DOCUMENTS

| | | | |
|---|---|---|---|
| EP | 0479210 | | 4/1992 |
| EP | 0708179 | | 4/1996 |
| EP | 0815135 | | 9/1996 |
| EP | 1695983 | B1 | 8/2006 |
| EP | 2036539 | A1 | 3/2009 |
| EP | 2036923 | A1 | 3/2009 |
| EP | 2398483 | | 8/2010 |
| EP | 2300035 | | 1/2012 |
| JP | 2003/192698 | | 7/2003 |
| WO | WO91/11457 | | 8/1991 |
| WO | WO96/29342 | | 9/1996 |
| WO | WO 9707814 | | 3/1997 |
| WO | 97/29180 | | 8/1997 |
| WO | WO9746584 | | 12/1997 |
| WO | 98/11126 | | 3/1998 |
| WO | 98/19698 | | 5/1998 |
| WO | WO 9824464 | | 6/1998 |
| WO | WO 9946283 | | 9/1999 |
| WO | WO99/67278 | | 12/1999 |
| WO | WO 0020592 | | 4/2000 |
| WO | 00/34331 | | 6/2000 |
| WO | WO00/42026 | | 7/2000 |
| WO | WO 0058360 | | 10/2000 |
| WO | 01/83527 | | 11/2001 |
| WO | WO 0181919 | | 11/2001 |
| WO | 01/98331 | | 12/2001 |
| WO | WO 0210195 | | 2/2002 |
| WO | WO0213801 | | 2/2002 |
| WO | 02/48183 | | 6/2002 |
| WO | WO 02100390 | | 12/2002 |
| WO | WO03/011892 | | 2/2003 |
| WO | 03/020201 | | 3/2003 |
| WO | WO03022304 | | 3/2003 |
| WO | WO 03026635 | | 4/2003 |
| WO | 03/035099 | | 5/2003 |
| WO | WO03/058203 | | 7/2003 |
| WO | WO 03082898 | | 10/2003 |
| WO | 03/103572 | | 12/2003 |
| WO | WO 03103697 | | 12/2003 |
| WO | WO 03105760 | | 12/2003 |
| WO | WO04000354 | | 12/2003 |
| WO | 2004/022004 | | 3/2004 |
| WO | 2004/067548 | | 8/2004 |
| WO | WO 2004078777 | | 9/2004 |
| WO | 2004/093823 | | 11/2004 |
| WO | 2004/105781 | | 12/2004 |
| WO | 2004/105790 | | 12/2004 |
| WO | WO 2004103390 | | 12/2004 |
| WO | WO 2005082928 | | 9/2005 |
| WO | WO 2006086769 | | 8/2006 |
| WO | WO 2006121904 | | 11/2006 |
| WO | WO2006124529 | | 11/2006 |
| WO | WO2006134340 | A2 | 12/2006 |
| WO | WO2007/124461 | | 1/2007 |
| WO | 2007/022123 | | 2/2007 |
| WO | WO 2007028632 | | 3/2007 |
| WO | WO2007028633 | | 3/2007 |
| WO | 2007/056362 | | 5/2007 |
| WO | 2007/100535 | | 9/2007 |
| WO | WO 2007109354 | | 9/2007 |
| WO | WO 2008021560 | | 2/2008 |
| WO | WO 2008022015 | | 2/2008 |
| WO | WO2008023050 | | 2/2008 |
| WO | WO 2008076933 | | 6/2008 |
| WO | 2008/086086 | | 7/2008 |
| WO | 2008/101017 | | 8/2008 |
| WO | WO2009030738 | A1 | 3/2009 |
| WO | WO2009030774 | A1 | 3/2009 |
| WO | WO2009034117 | A1 | 3/2009 |
| WO | WO2009034118 | A1 | 3/2009 |
| WO | WO2009034119 | A1 | 3/2009 |
| WO | WO2009035540 | A2 | 3/2009 |
| WO | 2009/058662 | | 5/2009 |
| WO | 2009/058734 | | 5/2009 |
| WO | 2009/059278 | | 5/2009 |
| WO | 2009/095479 | | 8/2009 |
| WO | 2009/099763 | | 8/2009 |
| WO | 2009/155257 | | 12/2009 |
| WO | 2009/155258 | | 12/2009 |
| WO | 2010/011439 | | 1/2010 |
| WO | 2010/071807 | | 6/2010 |
| WO | 2010/080605 | | 7/2010 |
| WO | 2010/096052 | | 8/2010 |
| WO | 2010/148089 | | 12/2010 |
| WO | 2011/075393 | | 6/2011 |
| WO | WO 2011087671 | | 7/2011 |
| WO | WO 2011087672 | | 7/2011 |
| WO | 2011/094337 | | 8/2011 |
| WO | WO2011119657 | | 9/2011 |
| WO | WO2011143208 | | 11/2011 |
| WO | WO2011143209 | | 11/2011 |
| WO | WO2011163012 | | 12/2011 |
| WO | WO2011163473 | | 12/2011 |

OTHER PUBLICATIONS

Andrews et al., "Forming Stable Helical Peptides Using Natural and Artificial Amino Acids", *Tetrahedron* 55: 11711-11743, (1999).

"Application of Chemical Biotechnology to Optimization of Endocrine Hormones," Carothers Lecture, Mar. 22, 2007.

Azizeh et al., "Pure glucagon antagonists: biological activities and cAMP accumulation using phosphodiesterase inhibitors," Peptides 1997, vol. 18, No. 5, pp. 633-641.

Azizeh et al., "The Role of Phylalanine at Position 6 in Glucagon's Mechanism of Biological Action: Multiple Replacement Analgues of Glucgon," J. Med. Chem., vol. 40, No. 16, 1997, pp. 2555-2562.

Azizeh et al., "Topographical amino acid substitution in position 10 of glucagon leads to antagonists/partial agonists with greater binding differences," J. Med. Chem., vol. 39, No. 13, Jun. 21, 1996, pp. 2449-2455.

Battersby et al., "Diketopiperazine Formation and N-Terminal Degradation in Recombinant Human Growth Hormone", *International Journal of Peptide & Protein Research* 44: 215-222, (1994).

Biotechnology—A Basis for Better Health & Economic Prosperity, Ohio State University presentation, Aug. 28, 2010.

"Biotechnology—A Basis for Better Health & Economic Prosperity," Indiana University television presentation, Nov. 2010.

Blache et al., "Development of an oxyntomodulin/glicentin C-terminal radioimmunoassay using a "thiol-maleoyl" coupling method for preparing the immunogen," Anal Biochem 1988 173(1):151-159 (1988), abstract only.

Chabenne et al., Optimization of the native glucagon sequence for medicinal purposes, J. Diabetes. Sci. Technol., 4(6): 1322-31, Nov. 1, 2010.

Chia et al., "Exogenous glucose-dependent insulinotropic polypeptide worsens post-prandial hyperglycemia in type 2 diabetes," Diabetes, 58: 1342-1349 (2009).

Collie et al., "Purification and sequence of rat oxyntomodulin," Proc. Natl. Acad. Sci. USA, vol. 91, pp. 9362-9366, Sep. 1994.

DatabaseEMBL, Jul. 16, 2007, Richard DiMarchi and David Smiley, "Human Glucagon Peptide SEQ ID No. 1," XP002631582, retrieved from EBI, Database Accession No. AGB07042, Abstract.

Jonathan Day et al., "A New Glucagon and GLP-1 Co-Agonist Eliminates Obesity in Rodents," Nature Chemical Biology, vol. 5, No. 10, Oct. 2009, pp. 749-757.

Day et al., Charge inversion at position 68 of the glucagon and glucagon-like peptide-1 receptors supports selectivity in hormone action. *J. Pept. Sci.*, 17(3): 218-25, Nov. 30, 2010.

Day, J.; Patterson, J.; Gelfanov, V. and DiMarchi, Richard Molecularbasis for Specificity in Biological Action at the Homologous Glucagon and GLP-1 Receptors, (2009) Proceedings of the 21st American Peptide Society 142-143.

(56) References Cited

OTHER PUBLICATIONS

De, Design of peptide-based prodrug chemistry and its application to glucagon-like peptide 1. Masters Thesis Aug. 2007. [Retrieved from the Internet on Jun. 16, 2009: <https://scholarworksiu.edu/dspace/browse?value=De%2C+ArnabBtype=author>]; p. 8, para 2; p. 16, para 3; p. 40, para 1; p. 66, para 2; p. 77, para 1-2; p. 79, para 1.

De, Arnab; DiMarchi, Richard D. Investigation of the feasibily of an amide-based prodrug under physiological conditions. International Journal of Peptide Research and Therapeutics (2008), 14(4), 393.

De, et al., "Investigation of the feasibily of an amide-based prodrug under physiological conditions," Int. J. Pept. Res. Ther., 14, pp. 255-262 (2008).

De, A. and DiMarchi, R. Synthesis & Analysis of Peptide Hormone-based prodrugs, (2009) Proceedings of the 21st American Peptide Society 160-161.

De, A. and DiMarchi, R. Synthesis & Characterization of Ester-Based Prodrugs of Glucagon-Like Peptide 1, Peptide Science (2010) 94(4) 448-456.

DiMarchi, "Peptides—Development of Prodrug Chemistry," RBF Symposium Feb. 1-4, 2011 India.

DiMarchi, Richard, "The Use of Bioproducts in the Treatments of Metabolic Diseases" presentation slides for the Keystone Symposia (Jan. 25, 2009, Banff, Alberta).

Drucker, "Glucagon Gene Expression in Vertebrate Brain," The Journal of Biological Chemistry, vol. 263, No. 27, pp. 13475-13478, 1988.

Drucker, "The biology of incretin hormones," Cell Metabolism 3:153-165 (2006).

"Emergence of Chemical Biotechnology," Eli Lilly and Co. presentation, Jun. 22, 2009.

"The Emergence of Chemical Biotechnology & Its Application to Optimization of Endocrine Hormones," UMBC presentation, Mar. 26, 2008.

Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).

Evans et al., "Effect of β-Endorphin C-Terminal Peptides on Glucose Uptake in Isolated Skeletal Muscles of the Mouse," Peptides, vol. 18, No. 1, pp. 165-167, (1997).

Extended EP Search Report completed by the EP Searching Authority on Apr. 6, 2011 in connection with EP Patent Application No. 08845852.6.

Marita P. Feldkaemper et al., "Localization and Regulation of Glucagon Receptors in the Chick Eye and Preproglucagon and Glucagon Receptor Expression in the Mouse Eye," Experimental Eye Research, Academic Press Ltd., London, vol. 79, No. 3, Sep. 1, 2004, pp. 321-329.

Finan, B.; Gelfanov, V. and DiMarchi, R. Assessment of a Tat-Derived Peptide as a Vector for Hormonal Transport, (2009) Proceedings of the 21st American Peptide Society 321-322.

Garcia-Aparicio et al., "Design and Discovery of a Novel Dipeptidyl-peptidase IV (CD26)-Based Prodrug Approach", *J. Med. Chem.* 49: 5339-5351 (2006).

Gelfanov, et al., Discover and Structural Optimization of High Affinity Co-Agonists at the Glucagon and GLP-1 Receptors, Understanding Biology Using Peptides, Springer, pp. 763-764, Jun. 23, 2005.

GenBank entry AAH05278. Jul. 15, 2006. [Retrieved from the Internet Jun. 18, 2009: ~http://www._ncbi._nim.n ih.gov/protein/13528972>].

Goolcharran et al., "Comparison of the Rates of Deamidation, Diketopiperazine Formation, and Oxidation in Recombinant Human Vascular Endothelial Growth Factor and Model Peptides", *AAPS Pharmsci 2000* 2(1) article 5: 1-6 (Mar. 17, 2000).

Gysin et al., "Design and Synthesis of Glucagon Partial Agonists and Antagonists," Biochemistry, 25, (1986), pp. 8278-8284.

Habegger et al., The metabolic actions of glucagon revisited, *Nat. Rev. Endocrinol.*, 6(12): 689-97, Oct. 19, 2010.

Habi, "Special Issue: Program and Abstracts for the 19th American Peptide Symposium, 2005, Abstracts of Poster Section C," (pp. 574-603) Article first published online: Jun. 10, 2005 I DOI: 10.1002/bip.20325.

Hansen et al., "Incretin hormones and insulin sensitivity," Trends in Endocrinology and Metabolism, vol. 16, No. 4, May/Jun. 2005, pp. 135-136.

Harris, J. Milton, Final Word: PEGylation—A "Sunset" Technology? <http://licence.icopyright.net/user/viewFreeUse.act?fuid=OTU1NjY3OA%3D%3D>, BioPharm International, Jun. 1, 2004.

Heppner et al., Glucagon regulation of energy metabolism, *Physiol Behav.*, 100(5): 545-8, Apr. 8, 2010.

Hjorth et al., "glucagon and Glucagon-like Peptide 1: Selective Receptor Recognition via Distinct Peptide Epitopes," The Journal of Biological Chemistry, vol. 269, No. 48, pp. 30121-30124, Dec. 2, 1994.

Hruby et al., "The Design and Biological Activities of Glucagon Agonists and Antagonists, and Their Use in Examining the Mechanisms of Glucose Action," *Curr. Med. Chem.-Imm., Endoc. & Metab. Agents*, 2001, 1, pp. 199-215.

Supplemental European Search Report issued in connection with EP Application No. 09800752 issued on Jun. 20, 2011.

Irwin et al., "Early administration of the glucose-dependent insulinotropic polypeptide receptor antagonist (Pro$^3$) GIP prevents the development of diabetes and related metabolic abnormalities associated with genetically inherited obesity in *ob/ob* mice," Diabetologia 50:1532-1540 (2007).

Joshi et al., "The Estimation of Glutaminyl Deamidation and Aspartyl Cleavage Rates in Glucagon," *International Journal of Pharmaceutics*, 273 (2004), pp. 213-219.

Joshi et al., "The Degradation Pathways of Glucagon in Acidic Solutions," *International Journal of Pharmaceutics*, 203 (2000), pp. 115-125.

Joshi et al, "Studies on the Mechanism of Aspartic Acid Cleavage and Glutamine Deamidation in the Acidic Degradation of Glucagon," *Journal of Pharmaceutical Sciences*, vol. 94, No. 9, Sep. 2005, pp. 1912-1927.

Krstenansky et al., "Importance of the C-terminal α-helical structure for glucagon's biological activity," Int. J. Peptide Protein Res., 32, 1988, 468-475.

Kukuch, A.; Patterson, J.; DiMarchi, R. and Tolbert, T. Immunoglobulin Fc-based Peptide Fusion Proteins as a Basis for Optimizing In Vivo Pharmacology, (2009) Proceedings of the 21$^{st}$ American Peptide Society 177-178.

Kulkarni, "GIP: No Longer the Neglected Incretin Twin?," Science Translational Medicine 2(49): p. 47, Sep. 15, 2010.

Lebl, Michal, "Peptides: Breaking Away: The Proceedings of the Twenty-First American Peptide Symposium", *Prompt Scientific Publishing* (2009).

Lee et al., "Synthesis, Characterization, and Pharmacokinetic Studies of PEGylated Glucagon-like Peptide-1," *Bioconjugate Chem.*, 2005, vol. 16, No. 2, pp. 377-382.

"Legacy Products—'Back to the Future'," presentation to Eli Lilly and Co., Sep. 22, 2005.

Levy et al., Optimization of the C-terminal Sequence in Glucagon to Maximize Receptor Affinity, *Understanding Biology Using Peptides*, American Peptide Society, Apr. 2006.

Levy et al., Optimization of the C-terminal Sequence in Glucagon to Maximize Receptor Affinity, Poster Presentation, Jun. 19, 2005.

Li et al., Crystallization and preliminary X-ray analysis of anti-obesity peptide hormone oxyntomodulin, *Protein & Peptide Letters*, 15(2): 232-4 (2008).

Li et al., Design, synthesis and crystallization of a novel glucagon analog as a therapeutic agent, *Acta Crystallogr. Sect. F Struct. Biol. Cryst. Commun.*, 63(Pt 7):599-601, Jun. 15, 2007.

Li et al., Structural Basis for Enhanced Solublity of a C-Terminally Extended Glucagon Analog, *Biopolymers.*, 96(4): 480 (2011).

Ma, T.; Day, J.; Gelfanov, V. and DiMarchi, R. Discovery and Structural Optimization of High Affinity Co-Agonists at the Glucagon and GLP-1 Receptors, (2009) Proceedings of the 21$^{st}$ American Peptide Society 146-147.

(56) References Cited

OTHER PUBLICATIONS

Madsen et al., "Structure—Activity and Protraction Relationship of Long-Acting Glucagon-like Peptide-1 Derivatives: Importance of Fatty acid Length, Polarity, and Bulkiness," J. Med. Chem. 2007, 50, pp. 6126-6132.
McKee et al., Receptor Binding and Adenylate Cyclase Activities of Glucagon Analogues Modified in the N-Terminal Region, Biochemistry, 25: 1650-6 (1986).
"Molecular Miracles," Indiana University, Apr. 13, 2011.
Montrose-Rafizadeh et al., "High Potency Antagonists of the Pancreatic Glucagon-like Peptide-1 Receptor," Journal of Biological Chemistry, 272(34) 21201-21206 (1997).
Murphy, et al., "Potent Long-Acting Alkylated Analogs of Growth Hormone-Releasing Factor," Pept. Res., vol. 1. No. 1, pp. 36-41 (1988).
Nogueiras et al., Direct control of peripheral lipid deposition by CNS GLP-1 receptor signaling is mediated by the sympathetic nervous system and blunted in diet-induced obesity, J. Neurosci., 29(18): 5916-25, May 6, 2009.
"Novel Glucagon Peptides That Demonstrate the Virtues of Combinatorial Pharmacology," University of Toledo, Mar. 22, 2012.
"Novel Glucagon-Based Peptides—Virtues of Combinatorial Pharmacology," Aug. 31, 2011, Berlin.
"Novel Glucagon-Based Peptides—Virtues of Combinatorial Pharmacology," European Peptide Symposium, Sep. 5-9, 2010, Copenhagen, Denmark.
"Novel Glucagon-Based Peptides—Virtues of Combinatorial Pharmacology," University of Michigan, Oct. 13, 2010.
"Novel Glucagon-Based Peptides—Virtues of Combinatorial Pharmacology," Yale University, May 13, 2011.
"Novel Glucagon-Like Chimera Peptides—Virtues of Combinatorial Pharmacology," AAPS May 2010.
"Novel Glucagon-Like Chimera Peptides—Virtues of Combinatorial Pharmacology," Keystone Conference, Apr. 12-17, 2010, Whistler, B.C.
"Novel Glucagon-Like Chimera Peptides—Virtues of Combinatorial Pharmacology," University of Cincinnati, Jun. 2010.
O'Brien, Assay for DPPIV Activity using Homogenous, Luminescent Method, Cell Notes 2005, 11:8-11.
Ouyang et al., Discovery of Bi-Functional Peptides Balanced in Glucagon Antagonism & GLP-1 Agonism. A Search for the Molecular Basis in the Inversion of Activity at Homologous Receptors, 71st Scientific sessions of American Diabetes Association 2011—Post-Conference Review and Analysis.
Ouyang et al., "Synthesis and Characterization of Peptides with Glucagon Antagonism and GLP-1 Agonism," poster presentation at the 21$^{st}$ American Peptide Symposium (Jun. 7-12, 2009, Bloomington, IN).
Pan et al., Design of a Long Acting Peptide Functioning as Both a Glucagon-like Peptide-1 Receptor Agonist and a Glucagon Receptor Agonist, J. Biol. Chem., 281(18): 12506-15, Table 1, May 5, 2006.
Pan et al., "Synthesis of Cetuximab-Immunoliposomes via a Cholesterol-Based Membrane Anchor for Targeting of EGFR," Bioconjugate Chem., 18, pp. 101-108, 2007.
Patterson et al., A novel human-based receptor antagonist of sustained action reveals body weight control by endogenous GLP-1, ACS Chem Biol., 6(2): 135-45 Nov. 4, 2010.
Patterson et al., Functional association of the N-terminal residues with the central region in glucagon-related peptides, J. Peptide Sci., First published online Jun. 10, 2011.
PCT International Search Report for PCT/US2008/050099 completed by the US Searching Authority on Sep. 1, 2008.
PCT International Search Report for PCT/US2008/053857 completed by the US Searching Authority on Sep. 16, 2008.
PCT International Search Report for PCT/US2011/041601 completed by the US Searching Authority on Nov. 10, 2011.
PCT International Search Report for PCT/US2008/081333 completed by the US Searching Authority on Mar. 12, 2009.
PCT International Search Report for PCT/US2006/043334 completed by the US Searching Authority on Apr. 23, 2009.
PCT International Search Report for PCT/US2008/080973 completed by the US Searching Authority on Jun. 6, 2009.
PCT International Search Report for PCT/US2009/031593 completed by the US Searching Authority on Jun. 18, 2009.
PCT International Search Report for PCT/US2009/034448 completed by the US Searching Authority on Jun. 4, 2010.
PCT International Search Report for PCT/US2009/047437 completed by the US Searching Authority on Nov. 3, 2009.
PCT International Search Report for PCT/US2009/047447 completed by the US Searching Authority on Mar. 19, 2010.
PCT International Search Report for PCT/US2009/068678 completed by the US Searching Authority on May 5, 2010.
PCT International Search Report for PCT/US2010/038825 completed by the US Searching Authority on Sep. 15, 2010.
PCT International Search Report for PCT/US2010/059724 completed by the US Searching Authority on Jun. 14, 2011.
"Novel Glucagon-Based Peptides—Virtues of Combinatorial Pharmacology," Peptides Therapeutics Symposium, Oct. 21-22, 2010, La Jolla, California.
"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.
Perret et al., "Mutational analysis of the glucagon receptor: similarities with the vasoactive intestinal peptide (VIP)/pituitary adenylate cyclase-activating peptide (PACAP)/secretin receptors for recognition of the ligand's third residue," J. Biochem., 362 (2002), pp. 389-394.
Phillips et al., "Supramolecular Protein Engineering: Design of Zinc-Stapled Insulin Hexamers as a Long Acting Depot," J. Biol. Chem., vol. 285, No. 16, Apr. 16, 2010, pp. 11755-11759.
Robberecht, P. et al., "Receptor Occupancy and Adenylate Cyclase Activation in Rat Liver and Heart Membranes by 10 Glucagon Analogs Modified in Position 2, 3, 4, 25, 27 and/or 29," Regulatory Peptides, 21 (1988), 117-128.
M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.
Santos et al., Cyclization-Activated Prodrugs. Synthesis, Reactivity and Toxicity of Dipeptide Esters of Paracetamol, Bioorganic & Medicinal Chemistry Letters 15: 1595-1598 (2005).
Sapse et al., The Role of Sale Bridge Formation in Glucagon: An Experimental and Theoretical Study of Glucagon Analogs and Peptide Fragments of Glucagon, Molec. Med., 8(5): 251-62, May 1, 2002.
Sato, H., "Enzymatic procedure for site-specific pegylation of proteins," Advanced Drug Delivery Reviews 54, pp. 487-504 (2002).
Schafmeister et al., "An All-Hydrocarbon Cross-Linking System for Enhancing the Helicity and Metaboli Stability of Peptides", J. Am. Chem. Soc. 122: 5891-5892 (2000).
"Speaking From the Gut: From Gastrointestinal Hormones to Combinatorial Therapies," Presentation to American Diabetes Association, Jun. 25, 2011.
Stigsnaes et al., "Characterisation and Physical Stability of PEGylated Glucagon," International Journal of Pharmaceutics, 330 (2007), pp. 87-98.
Sturm et al., "Structure-Function Studies on Positions 17, 18, and 21 Replacement Analogues of Glucagon: The Importance of Charged Residues and Salt Bridges in Glucagon Biological Activity," J Med Chem 1998, 41, 2693-2700.
Sueiras-Diaz et al., "Structure-Activity Studies on the N-Terminal Region of Glucagon," J. Med. Chem., 27, pp. 310-315, 1984.
Supplemental European Search Report issued in connection with EP Application No. 09767567.2 issued on Jun. 17, 2011.
"The Pursuit of Transformational Medicines," Keystone presentation, Jan. 29-Feb. 3, 2012, Santa Fe, NM.
"The Pursuit of Transformational Medicines," presentation to American Peptide Symposium, Jun. 25-30, 2011, San Diego, CA.
"The Pursuit of Transformational Medicines," NP2D presentation, Dec. 4, 2011.
Traylor et al., Identification of the High Potency Glucagon Agonist with Enhanced Biophysical Stability and Aqueous Solubility, Poster Abstract PY 10, pp. 505-506, Jun. 10, 2005.

(56) References Cited

OTHER PUBLICATIONS

Trivedi, D. et al., Design and synthesis of conformationally constrained glucagon analogues, *J. Med. Chem.*, 43(9): 1714-22, May 4, 2000 (Abstract).
Tschoep et al., A Novel Glucagon/GLP-1 Co-Agonist Eliminates Obesity in Rodents, Diabetes, 58 (Supp. 1): A83 (2009).
Tschoep, Matthias, "A Novel Glucagon/GLP-1 Co-Agonist Eliminates Obesity in Rodents" presentation slides for the 2009 American Diabetes Association meeting (Jun. 5-9, 2009, New Orleans, LA).
Tschoep et al., "A Novel Glucagon/GLP-1 Co-Agonist Eliminates Obesity in Rodents," American Diabetes Association Abstract No. 313-OR (2009).
Tschoep, Matthias, "Afferent Gut Hormones in the Control of Energy Balance and Metabolism" presentation slides for the 21st American Peptide Symposium (Jun. 7-12, 2009, Bloomington, IN).
Tschoep, "CNS Integration of Systems Metabolism: Target Opportunities for Diabetes Prevention and Therapy," RBF Symposium Feb. 1-4, 2011 India.
"Two for the Money" Gut Hormone Hybrids, Tschoep, ADA meeting, Jun. 25-29, 2010, Orlando, FL.
Unson et al., "Glucagon antagonists: Contribution to binding and activity of the amino-terminal sequence 1-5, position 12 and the putative alpha-helical segment 19-27," J. Biol. Chem. v264, pp. 789-794, Jan. 15, 1989, p. 792, para 1, Table 1.
Unson et al., Positively Charged Residues at Positions 12, 17, and 18 of Glucagon Ensure Maximum Biological Potency, *J. Biol. Chem.*, 273(17): 10308-12 (1998).
Unson et al., "Role of Histidine-1 in Glucagon Action," Archives of Biochemistry and Biophysics, vol. 300, No. 2, pp. 747-750, Feb. 1, 1993.
Vijayalakshmi et al., "Comparison of Helix-Stabilizing Effects of α, α-dialkyl Glycines with Linear and Cycloalkyl Side Chains", *Biopolymers* 53: 84-98 (Jan. 21, 2000).
Walensky et al., "Activation of Apoptosis in Vivo by a Hydrocarbon-Stapled BH3 Helix", *Science* 205: 1466-1470 (Sep. 3, 2004).
Ward, B.; Finan, B.; Gelfanov, V. and DiMarchi, R. Exploring the N-terminal Hydrophobic Faces of Glucagon and Glucagon-like Peptide-1, (2009) Proceedings of the 21$^{st}$ American Peptide Society 153-154.
Ward, "Fatty Acid Acylation of Peptides: Developing strategies to enhance medicines for treating metabolic disorders," Jan. 14, 2009.
Ward et al., In vitro and in vivo evaluation of native glucagon and glucagon analog (MAR-D28) during aging: lack of cytotoxicity and preservation of hyperglycemic effect, J. Diabetes Sci. Technol., 4(6):1311-21, Nov. 1, 2010.
Wibowo, Synthesis, Purification, and Biological Activity of AIB Substituted Glucagon and GLP-1 Peptide Analogues (2005-2006) vol. 45, 707=738, accessed https://scholarworks.iu.edu/dspce/handle/2022/326 on Jul. 17, 2012.
Wynne et al., "Subcutaneous Oxyntomodulin Reduces Body Weight in Overweight and Obese Subjects," *Diabetes*, vol. 54, Aug. 2005, pp. 2390-2395.
Yang, B. and DiMarchi, R.D. (2005). A Novel Approach to Resin-based Cysteine Alkylation Peptides: Chemistry, Structure and Biology, Proceedings of the XIX American Peptide Symposium, (88-89).
Yang et al., "A Novel Approach to Resin-Based Cysteine Alkylation," American Peptide Society, 2005.
Yang et al., "A Novel Approach to Resin-Based Cysteine Alkylation," poster presentation to American Peptide Society, 2005.
Yang et al., Synthesis and Biological Assessment of Sulfonic Acid-Based Glucagon Antagonists, Understanding Biology Using Peptides, American Peptide Symposia, 9(Part 6): 305-6 (2006).
Yang et al., "Synthesis and Biological Assessment of Sulfonic Acid-Based Glucagon Antagonists," American Peptide Society, 2005.
Yang et al., "Synthesis and Biological Assessment of Sulfonic Acid-Based Glucagon Antagonists," poster presentation to American Peptide Society, 2005.
Zhang et al., Design and synthesis of novel GLP1 analogues with significantly prolonged time action, Biopolymers., 80(4): 555 (2005).
Jen Holst "The Physiology of Glucagon-like Peptide-1", Physiological Reviews, V. 87, No. 4, pp. 1409-1439 (Oct. 2007).
Database Geneseq [Online] Feb. 16, 2012, Human glucagonanalog peptide SEQ:495, XP002710329, EBI accession No. GSP: AZQ99373, Database accession No. AZQ99373.
Azizeh et al., "The role of phenylalanine at position 6 in glucagon's mechanism of biological action: multiple replacement analogues of glucagon" J Med Chem 1997, 40, 2555-2562.
Supplemental EP Search report for EP09800752 completed on Jul. 20, 2011.
"Novel Glucagon-Like Chimera Peptides—Virtues of Combinatorial Pharmacology," AAPS 2005 San Francisco.
Zhou et al., "Peptide and protein drugs: I. Therapeutic applications, absorption and parenteral administration," International Journal of Pharmaceutics vol. 75 p. 97-111 (Sep. 20, 1991).

\* cited by examiner

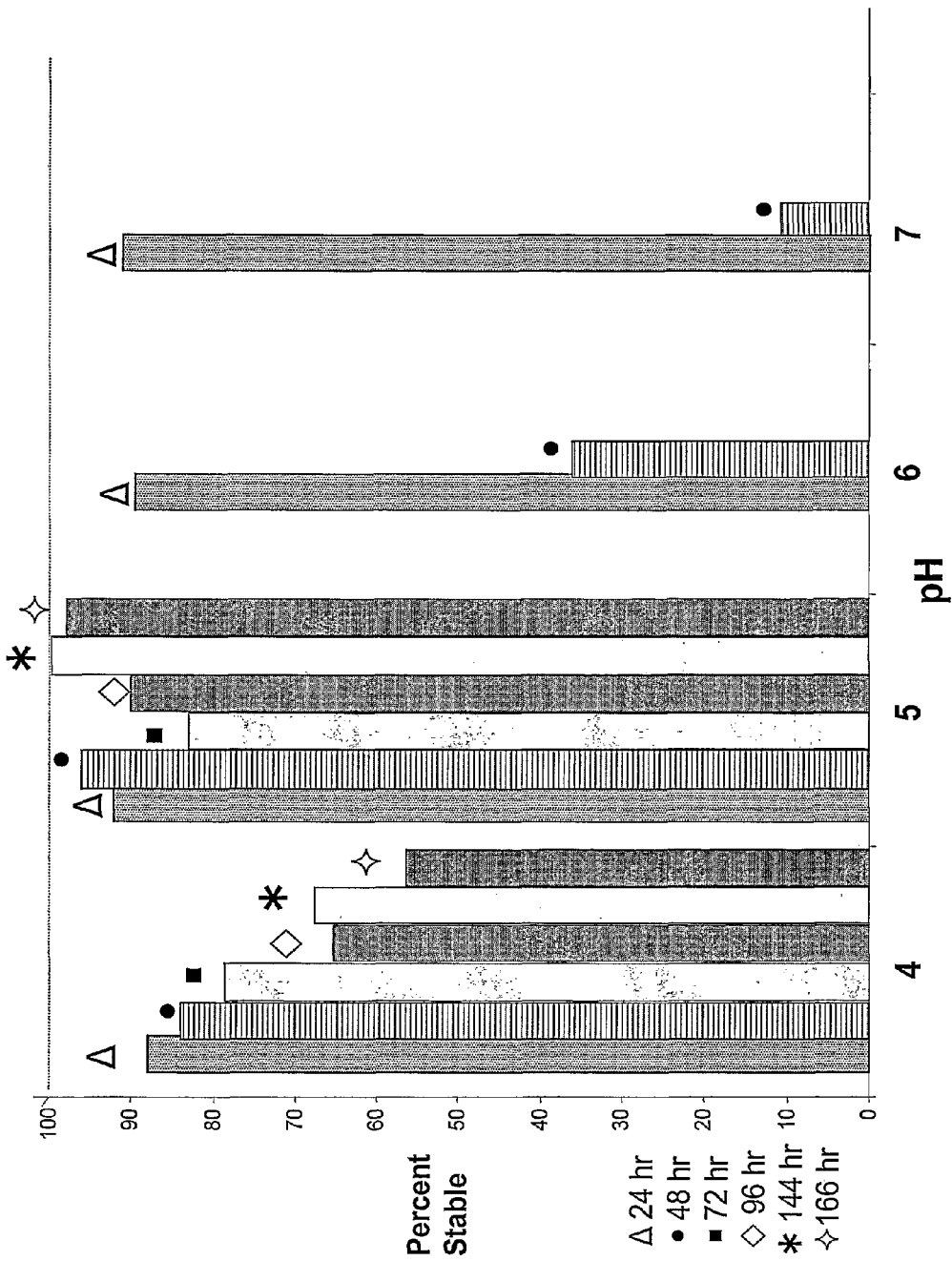
Fig. 1: Stability of Glucagon Cys$^{21}$-maleimidoPEG$_{5K}$ (37°C)

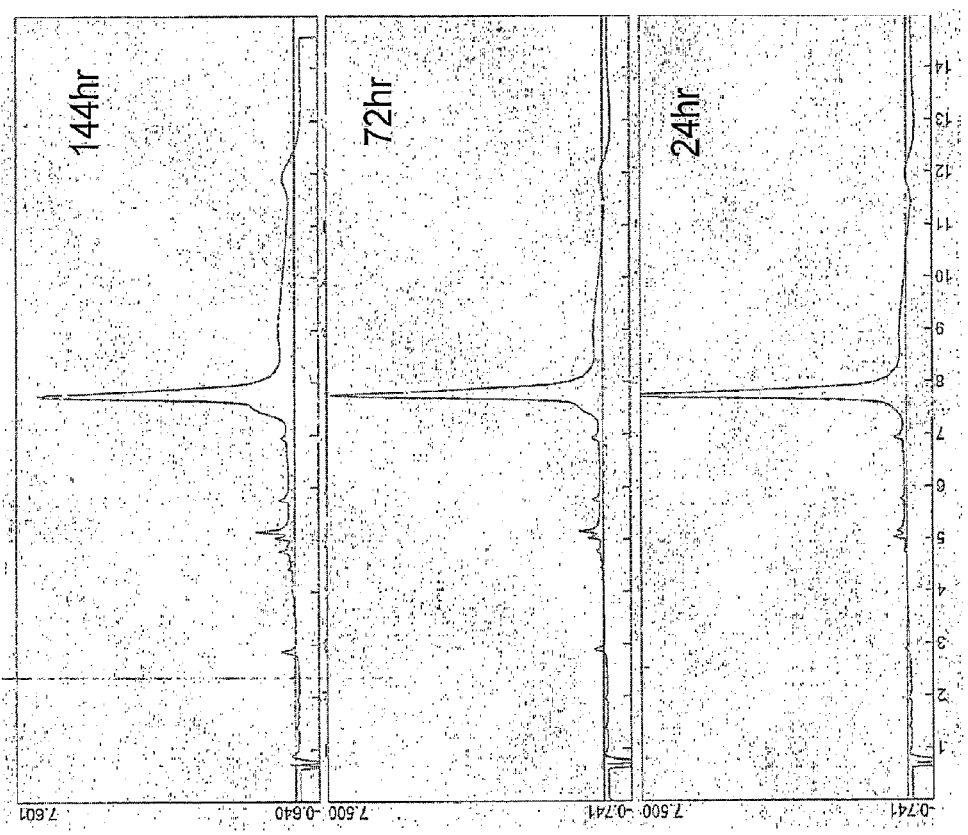

US 9,018,164 B2

GLUCAGON ANALOGS EXHIBITING PHYSIOLOGICAL SOLUBILITY AND STABILITY

CROSS REFERENCE TO RELATED APPLICATIONS

This application is a continuation of U.S. application Ser. No. 12/092,802, filed Aug. 25, 2008, now U.S. Pat. No. 8,338, 368 which is a 371 of International Application No. PCT/US2006/043334, filed Nov. 6, 2006, which claims priority to U.S. Provisional Application No. 60/734,307, filed Nov. 7, 2005, each application of which is incorporated herein by reference in its entirety.

BACKGROUND

Hypoglycemia occurs when blood glucose levels drops too low to provide enough energy for the body's activities. In adults or children older than 10 years, hypoglycemia is uncommon except as a side effect of diabetes treatment, but it can result from other medications or diseases, hormone or enzyme deficiencies, or tumors. When blood glucose begins to fall, glucagon, a hormone produced by the pancreas, signals the liver to break down glycogen and release glucose, causing blood glucose levels to rise toward a normal level. However for diabetics, this glucagon response to hypoglycemia may be impaired, making it harder for glucose levels to return to the normal range.

Hypoglycemia is a life threatening event that requires immediate medical attention. The administration of glucagon is an established medication for treating acute hypoglycemia and it can restore normal levels of glucose within minutes of administration. When glucagon is used in the acute medical treatment of hypoglycemia, a crystalline form of glucagon is solubilized with a dilute acid buffer and the solution is injected intramuscularly. While this treatment is effective, the methodology is cumbersome and dangerous for someone that is semi-conscious. Accordingly, there is a need for a glucagon analog that maintains the biological performance of the parent molecule but is sufficiently soluble and stable, under relevant physiological conditions, that it can be pre-formulated as a solution, ready for injection.

Additionally, diabetics are encouraged to maintain near normal blood glucose levels to delay or prevent microvascular complications. Achievement of this goal usually requires intensive insulin therapy. In striving to achieve this goal, physicians have encountered a substantial increase in the frequency and severity of hypoglycemia in their diabetic patients. Accordingly, improved pharmaceuticals and methodologies are needed for treating diabetes that are less likely to induce hypoglycemia than current insulin therapies.

As described herein, high potency glucagon agonists are provided that exhibit enhanced biophysical stability and aqueous solubility. These compounds can be used in accordance with one embodiment to prepare pre-formulated solutions ready for injection to treat hypoglycemia. Alternatively, the glucagon agonists can be co-administered with insulin to buffer the effects of insulin to allow for a more stable maintenance of blood glucose levels. In addition, other beneficial uses of compositions comprising the modified glucagon peptides disclosed herein are described in detail below.

SUMMARY

In accordance with one embodiment, analogs of glucagon are provided that have improved solubility and stability as well as similar bioactivies, including similar or higher potency and selectivity at the glucagon and GLP-1 receptors, relative to the native glucagon peptide. In one embodiment the glucagon analogs have at least 75% activity, or at least 85% activity as native glucagon. In one embodiment, the glucagon analogs of the present invention have potency greater than glucagon.

In accordance with one embodiment a glucagon agonist is provided comprising a glucagon peptide of SEQ ID NO: 45 or glucagon agonist derivative of SEQ ID NO: 45, wherein the side chain of an amino acid residue at position 21 or 24 of said glucagon peptide further comprises a hydrophilic moiety covalently bound to the amino acid residue. In accordance with one embodiment a glucagon agonist is provided comprising a glucagon peptide selected from the group consisting of SEQ ID NO: 2, SEQ ID NO: 3, and SEQ ID NO: 4, and glucagon agonist derivatives of SEQ ID NO: 2, SEQ ID NO: 3, and SEQ ID NO: 4, wherein the side chain of an amino acid residue at position 21 or 24 of said glucagon peptide further comprises a hydrophilic moiety covalently bound to the amino acid residue. The present invention further encompasses pharmaceutically acceptable salts of said glucagon agonists. In accordance with one embodiment the glucagon peptide is selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, and the hydrophilic moiety is a polyethylene glycol chain, having a molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of at least about 20,000 Daltons.

In another embodiment a glucagon agonist is provided comprising a glucagon peptide and a polyethylene glycol chain, wherein the polyethylene glycol chain is covalently bound to residue 16, 17, 20, 21, 24 or 29 of the glucagon peptide. The present invention also encompasses the pharmaceutically acceptable salts of said glucagon agonists. In one embodiment the polyethylene glycol chain is covalently linked to position 21 or 24 of the glucagon peptide and has a molecular weight selected from the range of about 500 to about 40,000 Daltons. In one embodiment the polyethylene glycol chain is covalently linked to position 21 or 24 of the glucagon peptide and has a molecular weight selected from the range of about 500 to about 5,000 Daltons. In another embodiment the polyethylene glycol chain has a molecular weight of at least about 20,000 Daltons. In one embodiment the glucagon peptide comprises the peptide selected from the group consisting of SEQ ID NO: 2, SEQ ID NO: 3, SEQ ID NO: 4, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and glucagon agonist derivatives thereof.

In accordance with one embodiment the glucagon peptides disclosed herein are modified by the addition of a second peptide to the carboxy terminus of the glucagon peptide. In one embodiment a glucagon peptide is covalently bound through a peptide bond to a second peptide, wherein the second peptide comprises a sequence selected from the group consisting of SEQ ID NO: 19, SEQ ID NO: 20 and SEQ ID NO: 21. In one embodiment the modified glucagon peptide comprises a peptide selected from the group consisting of SEQ ID NO: 24, SEQ ID NO: 25, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41, wherein a polyethylene glycol chain is bound at position 21 of SEQ ID NO: 24, SEQ ID NO: 25, SEQ ID NO: 34, SEQ ID NO: 36, SEQ ID NO: 38 and SEQ ID NO: 40, or bound at position 24 of SEQ ID NO: 32, SEQ ID NO: 33, SEQ ID NO: 35, SEQ ID NO: 37, SEQ ID NO: 39 and SEQ ID NO: 41, and has a molecular weight selected from the range of about 500 to about 40,000 Daltons.

In accordance with one embodiment a pharmaceutical composition is provided comprising the novel glucagon peptides disclosed herein. In one embodiment the pharmaceutical compositions comprise solutions that are sterilized and contained within various packages. The pharmaceutical compositions can be further packaged as part of a kit that includes a disposable device for administering the composition to a patient.

In accordance with one embodiment a method of rapidly treating hypoglycemia using a pre-formulated aqueous composition is provided. The method comprises the step of administering an effective amount of an aqueous solution comprising a novel modified glucagon peptide of the present disclosure. In one embodiment the glucagon peptide is pegylated at position 21 or 24 of the glucagon peptide and the PEG chain has a molecular weight of about 500 to about 5,000 Daltons. In one embodiment the modified glucagon solution is prepackaged in a device that is used to administer the composition to the patient suffering from hypoglycemia.

In accordance with one embodiment an improved method of regulating blood glucose levels in insulin dependent patients is provided. The method comprises the steps of administering insulin in an amount therapeutically effective for the control of diabetes and administering a novel modified glucagon peptide of the present disclosure in an amount therapeutically effective for the prevention of hypoglycemia, wherein said administering steps are conducted within twelve hours of each other. In one embodiment the glucagon peptide and the insulin are co-administered as a single composition, wherein the glucagon peptide is pegylated with a PEG chain having a molecular weight selected from the range of about 5,000 to about 40,000 Daltons In another embodiment a method is provided for inducing the temporary paralysis of the intestinal tract. The method comprises the step of administering one or more of the pegylated glucagon peptides disclosed herein to a patient.

In one embodiment a method of reducing weight gain or inducing weight loss is provided. The method comprises administering an effective amount of a composition comprising a glucagon agonist, wherein the glucagon agonist comprising a glucagon peptide selected from the group consisting of SEQ ID NO: 2, SEQ ID NO: 3, SEQ ID NO: 4, SEQ ID NO: 5, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, wherein amino acid 29 of the glucagon peptide is bound to a second peptide through a peptide bond, and said second peptide comprises the sequence of SEQ ID NO: 19, SEQ ID NO: 20 or SEQ ID NO: 21. In one embodiment the glucagon peptide is pegylated. In one embodiment the method comprises the step of administering a peptide comprising the sequence of SEQ ID NO: 24, SEQ ID NO: 25, SEQ ID NO: 32 or SEQ ID NO:33, wherein a polyethylene chain is covalently linked to amino acid position 21 of SEQ ID NO: 24 or 25, or at position 24 of SEQ ID NO: 32 or SEQ ID NO: 33.

BRIEF DESCRIPTION OF THE DRAWINGS

FIG. 1 is a bar graph representing the stability of Glucagon Cys$^{21}$-maleimidoPEG$_{5K}$ at 37° C. incubated for 24, 48, 72, 96, 144 and 166 hours, respectively.

FIG. 2 represents data generated from HPLC analysis of Glucagon Cys$^{21}$-maleimidoPEG$_{5K}$ at pH 5 incubated at 37° C. for 24, 72 or 144 hours, respectively.

DETAILED DESCRIPTION

Definitions

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of a glucagon peptide refers to a nontoxic but sufficient amount of the peptide to provide the desired effect. For example one desired effect would be the prevention or treatment of hypoglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

A "glucagon peptide" as used herein includes any peptide comprising, either the amino acid sequence of SEQ ID NO: 1, or any derivative of the amino acid sequence of SEQ ID NO: 1, including amino acid substitutions, or post translational modifications (e.g. methylation, acylation, ubiquitination and the like) of the peptide, that stimulates glucagon or GLP-1 receptor activity, as measured by cAMP production using the assay described in Example 13.

The term "glucagon agonist" refers to a complex comprising a glucagon peptide.

As used herein a "glucagon agonist derivative" is a glucagon peptide that has been modified to include one or more conservative amino acid substitutions at one or more of positions 2, 5, 7, 10, 11, 12, 13, 14, 16, 17, 18, 19, 20, 21, 24, 27, 28 or 29.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine As used herein the general term "polyethylene glycol" or "PEG", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 40,000 Daltons. "polyethylene glycol" or "PEG" is used in combination with a numeric suffix to indicate the approximate average molecular weight thereof. For example, PEG-5,000 refers to polyethylene glycol having a total molecular weight average of about 5,000.

As used herein the term "pegylated" and like terms refers to a compound that has been modified from its native state by linking a polyethylene glycol polymer to the compound. A "pegylated glucagon peptide" is a glucagon peptide that has a PEG chain covalently bound to the glucagon peptide.

As used herein a general reference to a peptide is intended to encompass peptides that have modified amino and carboxy termini. For example, an amino acid chain comprising an amide group in place of the terminal carboxylic acid is intended to be encompassed by an amino acid sequence designating the standard amino acids.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein a "dimer" is a complex comprising two subunits covalently bound to one another via a linker. The term dimer, when used absent any qualifying language, encompasses both homodimers and heterodimers. A homodimer comprises two identical subunits, whereas a heterodimer comprises two subunits that differ, although the two subunits are substantially similar to one another.

Embodiments

One embodiment of the present invention is directed to a glucagon agonist that has been modified relative to the wild type peptide of His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1) to improve the peptides solubility and stability in aqueous solutions at physiological pH, while retaining the native peptide's biological activity. In accordance with one embodiment, applicants have found that introduction of hydrophilic groups at positions 16, 17, 20, 21, 24 and 29 of the native peptide can improve the solubility and stability of the resulting glucagon analog in solutions having a physiological pH. More particularly, in one embodiment the glucagon peptide is modified to comprise one or more hydrophilic groups covalently linked to the side chains of amino acids present at positions 21 and 24 of the glucagon peptide, and in one embodiment the hydrophilic group is PEG. In one embodiment the glucagon peptide comprises a sequence selected from the group consisting of SEQ ID NO: 45 and glucagon agonist derivatives of SEQ ID NO: 45, with the proviso that when the amino acid at position 21 is Asp the amino acid at position 24 is not Gln, and when the amino acid at position 24 is Gln the amino acid at position 21 is not Asp, wherein one or more hydrophilic groups covalently linked to the side chains of amino acids present at positions 21 and 24 of the glucagon peptide, and in one embodiment the hydrophilic group is PEG.

In accordance with one embodiment, the native glucagon peptide of SEQ ID NO: 1 is modified to contain one or more amino acid substitution at positions 16, 17, 20, 21, 24 and/or 29, wherein the native amino acid is substituted with an amino acid having a side chain suitable for crosslinking with hydrophilic moieties, including for example, PEG. The native peptide can be substituted with a naturally occurring amino acid or a synthetic (non-naturally occurring) amino acid. Synthetic or non-naturally occurring amino acids refer to amino acids that do not naturally occur in vivo but which, nevertheless, can be incorporated into the peptide structures described herein.

In one embodiment, a glucagon agonist is provided wherein the native glucagon peptide sequence has been modified to contain a naturally occurring or synthetic amino acid in at least one of positions 16, 17, 20, 21, 24 and 29 of the native sequence, wherein the amino acid substitute further comprises a hydrophilic moiety. In one embodiment one or more amino acids at position 16, 17, 20, 21, 24 and 29 of the native peptide are substituted with an amino acid selected from the group consisting of lysine, cysteine, ornithine, homocysteine and acetyl phenylalanine, wherein the substituting amino acid further comprises a hydrophilic moiety covalently bound to the side chain of the amino acid. In one embodiment the substitution is at position 21 or 24, and in a further embodiment the hydrophilic moiety is a PEG chain.

In one embodiment the native glucagon peptide is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, the native glucagon peptide is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol.

It has been reported that certain positions of the native glucagon peptide can be modified while retaining at least some of the activity of the parent peptide. Accordingly, one or more of the amino acids located at positions at positions 2, 5, 7, 10, 11, 12, 13, 14, 16, 17, 18, 19, 20, 21, 24, 27, 28 or 29 of the peptide of SEQ ID NO: 1 can be substituted with an amino acid different from that present in the native glucagon peptide, and still retain the biological activity of the native glucagon. In accordance with one embodiment the lysine residue at position 12 of the native peptide is substituted with arginine and a single lysine substitution is inserted for the amino acid present at position 16, 17, 20, 21, 24 or 29. In another embodiment the methionine residue present at position 27 of the native peptide is changed to leucine or norleucine to prevent oxidative degradation of the peptide.

In one embodiment a glucagon peptide is provided that comprises a polyethylene glycol chain covalently bound to the side chain of an amino acid present at position 16, 17, 20, 21, 24 or 29, wherein the glucagon peptide further comprises one, two or three amino acid substitutions at positions selected from positions 2, 5, 7, 10, 11, 12, 13, 14, 16, 17, 18, 19, 20, 21, 24, 27, 28 or 29. In one embodiment the substitutions at positions 2, 5, 7, 10, 11, 12, 13, 14, 16, 17, 18, 19, 20, 27, 28 or 29 are conservative amino acid substitutions. In one embodiment the amino acid present at position 16, 17, 20, 21, 24 or 29 of the native peptide is substituted with cysteine or lysine. However, in one embodiment an amino acid substitution (using a natural or synthetic amino acid) is made at position 16, 17, 20, 21, 24 or 29, wherein the substitute amino acid allows for the covalent attachment of a PEG chain to the amino acid side chain. In one embodiment the substitution is made at position 21 and/or 24.

In one embodiment an improved glucagon agonist is provided having superior stability and solubility in aqueous solutions at physiological pH. In this embodiment the glucagon peptide is modified to comprise a polyethylene glycol chain linked to an amino acid side chain of an amino acid located at positions 2, 5, 7, 10, 11, 12, 13, 14, 16, 17, 18, 19, 20, 27, 28 or 29 of the native peptide. More particularly, in one embodiment the polyethylene glycol chain is covalently bound to an amino acid side chain at position 16, 17, 20, 21, 24 or 29 of the glucagon peptide, in one embodiment the polyethylene glycol chain is bound to an amino acid side chain at position 16, 21 or 24, and in one embodiment the polyethylene glycol chain is covalently bound to the side chain of amino acid 21 or 24.

The polyethylene glycol chain may be in the form of a straight chain or it may be branched. In accordance with one embodiment the polyethylene glycol chain has an average molecular weight selected from the range of about 500 to about 10,000 Daltons. In one embodiment the polyethylene glycol chain has an average molecular weight selected from the range of about 1,000 to about 5,000 Daltons. In one embodiment the polyethylene glycol chain has an average molecular weight selected from the range of about 2,000 to about 5,000 Daltons. In one embodiment the polyethylene glycol chain has an average molecular weight selected from the range of about 4,000 to about 5,000 Daltons.

In accordance with one embodiment the modified glucagon peptide comprises two or more polyethylene chains covalently bound to the glucagon peptide wherein the total molecular weight of the glucagon chains is about 1,000 to about 5,000 Daltons. In one embodiment the pegylated glucagon agonist comprises a peptide selected from the group consisting of SEQ ID NO: 12, SEQ ID NO: 22 and SEQ ID NO: 23 or a glucagon agonist derivative of SEQ ID NO: 12, SEQ ID NO: 22 or SEQ ID NO: 23, wherein a PEG chain is covalently linked to the amino acid residue at position 21 and at position 24, and wherein the combined molecular weight of the two PEG chains is about 1,000 to about 5,000 Daltons.

In accordance with one embodiment a glucagon agonist is provided comprising a modified glucagon peptide selected from the group consisting of:

```
                                          (SEQ ID NO: 5)
NH2-His-Ser-Gln-Gly-Thr-Phe-Thr-Ser-Asp-Tyr-Ser-

Lys-Tyr-Leu-Asp-Ser-Arg-Arg-Ala-Gln-Asp-Phe-Val-

Gln-Trp-Leu-Leu-Asn-Thr (SEQ ID NO: 44)
NH2-His-Ser-Gln-Gly-Thr-Phe-Thr-Ser-Asp-Tyr-Ser-

Lys-Tyr-Leu-Asp-Ser-Arg-Arg-Ala-Gln-Asp-Phe-Val-

Gln-Trp-Leu-Nle-Asn-Thr (SEQ ID NO: 2)
NH2-His-Ser-Gln-Gly-Thr-Phe-Thr-Ser-Asp-Tyr-Ser-

Xaa-Tyr-Leu-Asp-Ser-Arg-Arg-Ala-Gln-Xaa-Phe-Val-

Gln-Trp-Leu-Xaa-Asn-Thr-R, (SEQ ID NO: 3)
NH2-His-Ser-Gln-Gly-Thr-Phe-Thr-Ser-Asp-Tyr-Ser-

Xaa-Tyr-Leu-Asp-Ser-Arg-Arg-Ala-Gln-Asp-Phe-Val-

Xaa-Trp-Leu-Xaa-Asn-Thr-R
and
                                          (SEQ ID NO: 4)
NH2-His-Ser-Gln-Gly-Thr-Phe-Thr-Ser-Asp-Tyr-Ser- Xaa-Tyr-Leu-Asp-Ser-Arg-Arg-Ala-Gln-Xaa-Phe-Val- Xaa-Trp-Leu-Xaa-Asn-Thr-R,
``` wherein Xaa at position 12=Lys or Arg, Xaa at positions 21 and 24 are independently selected from the group consisting of Lys, Cys, Orn, homocysteine and acetyl phenylalanine, Xaa at position 27=Met, Leu or Nle, and R is COOH or CONH$_2$, wherein the peptide is pegylated at position 21 for SEQ ID NO: 2, position 24 for SEQ ID NO: 3 and at positions 21 and 24 of SEQ ID NO: 4. In accordance with one embodiment Xaa at position 27 for SEQ ID NO: 2, SEQ ID NO: 3, and SEQ ID NO: 4 is Leu or Nle. In accordance with one embodiment the peptide comprises SEQ ID NO: 2 or SEQ ID NO: 3. In accordance with one embodiment the peptide comprises a sequence selected from the group consisting of SEQ ID NO: 10, SEQ ID NO: 11, SEQ ID NO: 13, SEQ ID NO: 14, SEQ ID NO: 15, SEQ ID NO: 16, SEQ ID NO: 17 and SEQ ID NO: 18, wherein the peptide is pegylated at position 21 for SEQ ID NO: 10, SEQ ID NO: 13, SEQ ID NO: 15 and SEQ ID NO: 17, and pegylated at position 24 for SEQ ID NO: 11, SEQ ID NO: 14, SEQ ID NO: 16 and SEQ ID NO: 18. In one embodiment the glucagon agonist comprises the peptide of SEQ ID NO: 6, SEQ ID NO: 7, SEQ ID NO: 8 and SEQ ID NO: 9. In one embodiment the terminal amino acid of the glucagon peptides of the present invention have an amide group in place of the carboxylic acid group that is present on the native amino acid.

As described in detail in the Examples, the glucagon agonists of the present invention have enhanced biophysical stability and aqueous solubility while retaining the bioactivity of the native peptide, both in terms of potency and selectivity at the glucagon and GLP-1 receptors. Accordingly, the glucagon agonists of the present invention are believed to be suitable for any use that has previously been described for the native glucagon peptide. Accordingly, the modified glucagon peptides described herein can be used to treat hypoglycemia, to induce temporary paralysis of the gut for radiological uses, to reduce and maintain body weight, or treat other metabolic diseases that result from low blood levels of glucagon.

One aspect of the present disclosure is directed to a preformulated aqueous solution of the presently disclosed glucagon agonist for use in treating hypoglycemia. The improved stability and solubility of the agonist compositions described herein allow for the preparation of pre-formulated aqueous solutions of glucagon for rapid administration and treatment of hypoglycemia. In one embodiment a solution comprising a pegylated glucagon agonist is provided for administration to a patient suffering from hypoglycemia, wherein the total molecular weight of the PEG chains linked to the pegylated glucagon agonist is between about 500 to about 5,000 Daltons. In one embodiment the pegylated glucagon agonist comprises a peptide selected from the group consisting of SEQ ID NO: 2, SEQ ID NO: 3, and SEQ ID NO: 4, and glucagon agonist derivatives of SEQ ID NO: 2, SEQ ID NO: 3, and SEQ ID NO: 4, wherein the side chain of an amino acid residue at position 21 and/or 24 of said glucagon peptide is covalently bound to the polyethylene glycol chain. In one embodiment, the pegylated glucagon agonist comprises the peptide of SEQ ID NO: 2, wherein the amino acid residue at position 21 of the peptide is covalently linked to polyethylene glycol. In one embodiment, the pegylated glucagon agonist comprises the peptide of SEQ ID NO: 3, wherein the amino acid residue at position 24 of the peptide is covalently linked to polyethylene glycol. In another embodiment the pegylated glucagon agonist comprises the peptide of SEQ ID NO: 7 or SEQ ID NO. 8. In a further embodiment, the pegylated glucagon agonist comprises the peptide of SEQ ID NO: 22 or SEQ ID NO: 23, wherein a PEG chain is covalently linked to the amino acid residue at position 21 and at position 24, wherein the combined molecular weight of the two PEG chains is about 1,000 to about 5,000 Daltons.

The method of treating hypoglycemia in accordance with the present invention comprises the steps of administering the presently disclosed glucagon agonists to a patient using any standard route of administration, including parenterally, such as intravenously, subcutaneously or intramuscularly, transdermally, rectally, orally, nasally or by inhalation. In one embodiment the composition is administered subcutaneously or intramuscularly. In one embodiment, the composition is administered parenterally and the glucagon composition is prepackaged in a syringe. In one embodiment the glucagon composition to be administered to treat an individual suffering from hypoglycemia is provided as two separated solutions. The first solution comprises the glucagon agonist in an aqueous solution at a pH of about 4.5 to about 5.5. In one embodiment the first solution has a pH of about 5.0. The second aqueous solution is at a pH greater than 7.0 such that when the first solution is mixed with the second solution the pH of the resulting mixture is approximately at physiological pH. In one embodiment, after mixture of the first and second solutions, the pH of the resulting mixture is about 7.4. In one embodiment the first and second solutions are contained within a single vessel and separated from one another by a valve or seal wherein upon opening of the valve, or breakage of the seal, the two solutions mix to provide a composition comprising a glucagon peptide and pharmaceutically acceptable carrier wherein the pH of the composition is at a physiologically acceptable pH. In this manner the vessel comprising the two solutions can be stored for long periods of time. At a time of need the two solutions can be mixed and rapidly administered to the patient.

Surprisingly, applicants have discovered that pegylated glucagon peptides can be prepared that retain the parent peptide's bioactivity and specificity. However, increasing the length of the PEG chain, or attaching multiple PEG chains to the peptide, such that the total molecular weight of the linked PEG is greater than 5,000 Daltons, begins to delay the time action of the modified glucagon. In accordance with one embodiment, a glucagon peptide is provided wherein the peptide comprises one or more polyethylene glycol chains, wherein the total molecular weight of the linked PEG is greater than 5,000 Daltons, and in one embodiment is greater than 10,000 Daltons. Such modified glucagon peptides have a delayed time of activity but without loss of the bioactivity. Accordingly, such compounds can be administered prophylactically to extend the effect of the administered glucagon peptide.

In one embodiment the pegylated glucagon agonist comprises a peptide selected from the group consisting of SEQ ID NO: 2, SEQ ID NO: 3 and SEQ ID NO: 4, and glucagon agonist derivatives of SEQ ID NO: 2, SEQ ID NO: 3 and SEQ ID NO: 4, wherein the side chain of an amino acid residue at position 21 and/or 24 of said glucagon peptide is covalently bound to one or more polyethylene glycol chains having a combined molecular weight of greater than about 10,000 Daltons, and in one embodiment the molecular weight of the PEG chain(s) is greater than 10,000 and less than or equal to 40,000 Daltons. In one embodiment, the pegylated glucagon agonist comprises the peptide of SEQ ID NO: 2, wherein an amino acid residue at position 21 of the peptide is covalently linked to a polyethylene glycol chain having a molecular weight selected from the range of about 10,000 to about 40,000 Daltons. In one embodiment, the pegylated glucagon agonist comprises the peptide of SEQ ID NO: 3, and wherein an amino acid residue at position 24 of the peptide is covalently linked to a polyethylene glycol chain having a molecular weight selected from the range of about 10,000 to about 40,000 Daltons. In another embodiment the pegylated glucagon agonist comprises the peptide of SEQ ID NO: 7 or SEQ ID NO. 8, wherein the covalently linked PEG chain has a molecular weight of at least about 10,000 Daltons, and in one embodiment the molecular weight of the PEG is selected from the range of about 20,000 to about 40,000 Daltons. In another embodiment the pegylated glucagon agonist comprises the peptide of SEQ ID NO: 22 or SEQ ID NO: 23, wherein a PEG chain is covalently linked to the amino acid residue at position 21 and at position 24, wherein the combined molecular weight of the two PEG chains is at least about 10,000 Daltons.

Glucagon peptides that have been modified to be covalently bound to a PEG chain having a molecular weight of greater than 10,000 Daltons can be administered in conjunction with insulin to buffer the actions of insulin and help to maintain stable blood glucose levels in diabetics. The modified glucagon peptides of the present disclosure can be co-administered with insulin as a single composition, simultaneously administered as separate solutions, or alternatively, the insulin and the modified glucagon peptide can be administered at different time relative to one another. In one embodiment the composition comprising insulin and the composition comprising the modified glucagon peptide are administered within 12 hours of one another. The exact ratio of the modified glucagon peptide relative to the administered insulin will be dependent in part on determining the glucagon levels of the patient, and can be determined through routine experimentation.

In accordance with one embodiment an aqueous solution is provided comprising insulin and a modified glucagon peptide, wherein the glucagon peptide comprises a polyethylene glycol chain covalently bound to an amino acid side chain at position 16, 17, 20, 21, 24 or 29. In one embodiment the molecular weight of the PEG chain of the modified glucagon peptide is greater than 10,000 Daltons. In one embodiment the pegylated glucagon peptide comprises a peptide selected from the group consisting of SEQ ID NO: 2 and SEQ ID NO: 3 wherein the side chain of an amino acid residue at position 21 or 24 of said glucagon peptide is covalently bound to the polyethylene glycol chain. In one embodiment, the pegylated glucagon agonist comprises the peptide of SEQ ID NO: 2, wherein an amino acid residue at position 21 of the peptide is covalently linked to a polyethylene glycol chain having a molecular weight of about 10,000 to about 40,000. In one embodiment, the pegylated glucagon agonist comprises the peptide of SEQ ID NO: 3, wherein an amino acid residue at position 24 of the peptide is covalently linked to a polyethylene glycol chain having a molecular weight of about 10,000 to about 40,000. In another embodiment the pegylated glucagon agonist comprises the peptide of SEQ ID NO: 7 or SEQ ID NO. 8.

The present disclosure also encompasses glucagon fusion peptides wherein a second peptide has been fused to the c-terminus of the glucagon peptide. More particularly, the fusion glucagon peptide may comprise a glucagon agonist derivative of SEQ ID NO: 1 further comprising an amino acid sequence of SEQ ID NO: 19 (GPSSGAPPPS), SEQ ID NO: 20 (KRNRNNIA) or SEQ ID NO: 21 (KRNR) linked to amino acid 29 of the glucagon peptide. In one embodiment the amino acid sequence of SEQ ID NO: 19 (GPSSGAPPPS), SEQ ID NO: 20 (KRNRNNIA) or SEQ ID NO: 21 (KRNR) is bound to amino acid 29 of the glucagon peptide through a peptide bond. In one embodiment the glucagon peptide portion of the glucagon fusion peptide is selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18 wherein the PEG chain, when present, is selected from the range of 500 to 40,000 Daltons. More particularly, in one embodiment the glucagon peptide segment is selected from the group consisting of SEQ ID NO: 7 and SEQ ID NO: 8 wherein the PEG chain is selected from the range of 500 to 5,000. In one embodiment the glucagon fusion peptide comprises the sequence of SEQ ID NO: 22 or SEQ ID NO: 23. In one embodiment the glucagon fusion peptide comprises the sequence of SEQ ID NO: 24, SEQ ID NO: 25, SEQ ID NO: 32 or SEQ ID NO: 33, wherein a polyethylene chain of about 500 to 5,000 Daltons is covalently linked to amino acid position 21 of SEQ ID NO: 24 or 25, or at position 24 of SEQ ID NO: 32 or SEQ ID NO: 33.

In one embodiment a glucagon fusion peptide is provided comprising a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, covalently linked to the sequence of SEQ ID NO: 19 (GPSSGAPPPS) or SEQ ID NO: 21, wherein the PEG chain, when present, is selected from the range of 500 to 40,000 Daltons. In one embodiment the fusion peptide comprises a glucagon peptide selected from the group consisting of SEQ ID NO: 1, SEQ ID NO: 7, SEQ ID NO: 8, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18 covalently linked to the sequence of SEQ ID NO: 19 (GPSSGAPPPS) or SEQ ID NO: 21. In another embodiment the fusion peptide comprises a glucagon peptide selected from the group consisting of SEQ ID NO: 7 and SEQ ID NO: 8, SEQ ID NO: 10, SEQ ID NO: 11, SEQ ID NO: 17 and SEQ ID NO: 18 covalently linked to the sequence of SEQ ID NO: 19 (GPSSGAPPPS) or SEQ ID NO: 21.

In one embodiment the composition comprises a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18 covalently linked to the sequence of SEQ ID NO: 20 (KRNRNNIA). In one embodiment the fusion peptide comprises a glucagon peptide selected from the group consisting of SEQ ID NO: 7, SEQ ID NO: 8, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18 covalently linked to the sequence of SEQ ID NO: 20 (KRNRNNIA). In another embodiment the fusion peptide comprises a glucagon peptide selected from the group consisting of SEQ ID NO: 7, SEQ ID NO: 8, SEQ ID NO: 10, SEQ ID NO: 11, SEQ ID NO: 17 and SEQ ID NO: 18 covalently linked to the sequence of SEQ ID NO: 20 (KRNRNNIA).

In accordance with one embodiment the modified glucagon peptides disclosed herein are used to induce temporary paralysis of the intestinal tract. This method has utility for radiological purposes and comprises the step of administering an effective amount of a pharmaceutical composition comprising a pegylated glucagon peptide, a glucagon peptide comprising a c-terminal extension or a dimer of such peptides. In one embodiment the glucagon peptide comprises a sequence selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18 wherein a PEG chain, of about 1,000 to 40,000 Daltons is covalently bound to an amino acid residue at position 21 or 24. In one embodiment the glucagon peptide is selected from the group consisting of SEQ ID NO: 7, SEQ ID NO: 8, SEQ ID NO: 10, SEQ ID NO: 11, SEQ ID NO: 17 and SEQ ID NO: 18. In one embodiment the PEG chain has a molecular weight of about 500 to about 5,000 Daltons.

In a further embodiment the composition used to induce temporary paralysis of the intestinal tract comprises a first modified glucagon peptide and a second modified glucagon peptide, wherein the first modified peptide comprises a covalently linked PEG chain of about 500 to about 5,000 Daltons and the second peptide comprises a covalently linked PEG chain of about 10,000 to about 40,000 Daltons. In this embodiment the PEG chain of each peptide is covalently bound to an amino acid residue at either position 21 or 24 of the respective peptides, and independent of one another.

Oxyntomodulin, a naturally occurring digestive hormone found in the small intestine, has been reported to cause weight loss when administered to rats or humans (see Diabetes 2005; 54:2390-2395). Oxyntomodulin is a 37 amino acid peptide that contains the 29 amino acid sequence of glucagon (i.e. SEQ ID NO: 1) followed by an 8 amino acid carboxy terminal extension of SEQ ID NO: 20 (KRNRNNIA). Accordingly, applicants believe that the bioactivity of oxyntomodulin can be retained (i.e. appetite suppression and induced weight loss/weight maintenance), while improving the solubility and stability of the compound and improving the pharmacokinetics, by substituting the glucagon peptide portion of oxyntomodulin with the modified glucagon peptides disclosed herein. In addition applicants also believe that a truncated Oxyntomodulin molecule, having the terminal four amino acids removed will also be effective in suppressing appetite and inducing weight loss/weight maintenance.

Accordingly, the present invention also encompasses the modified glucagon peptides of the present invention that have a carboxy terminal extension of SEQ ID NO: 20 (KRNRN-NIA) or SEQ ID NO: 21. In accordance with one embodiment a glucagon agonist derivative of SEQ ID NO: 1 further comprising the amino acid sequence of SEQ ID NO: 20 (KRN-RNNIA) or SEQ ID NO: 21 is linked to amino acid 29 of the glucagon peptide is administered to individuals to induce weight loss or prevent weight gain. In another embodiment a method of reducing weight gain or inducing weight loss in an individual comprises administering an effective amount of a composition comprising a glucagon agonist comprising a glucagon peptide selected from the group consisting of SEQ ID NO: 2, SEQ ID NO: 3 or SEQ ID NO: 4, wherein amino acid 29 of the glucagon peptide is bound to a second peptide through a peptide bond, and said second peptide comprises the sequence of SEQ ID NO: 20 (KRNRNNIA) or SEQ ID NO: 21. In one embodiment the glucagon peptide segment of the glucagon agonist is selected from the group consisting of SEQ ID NO: 10, SEQ ID NO: 11, SEQ ID NO: 13, SEQ ID NO: 14, SEQ ID NO: 15, SEQ ID NO: 16, SEQ ID NO: 17 and SEQ ID NO: 18, wherein a PEG chain of about 1,000 to 40,000 Daltons is covalently bound to an amino acid residue at position 21 or 24. In one embodiment the glucagon peptide segment is selected from the group consisting of SEQ ID NO: 7, SEQ ID NO: 8, SEQ ID NO: 10, SEQ ID NO: 11, SEQ ID NO: 17 and SEQ ID NO: 18 wherein the molecular weight of the PEG chain is selected from the range of 1,000 to 40,000 Daltons. More particularly, in one embodiment the glucagon peptide segment of the glucagon fusion peptide is selected from the group consisting of SEQ ID NO: 7 and SEQ ID NO: 8 wherein the molecular weight of the PEG chain is selected from the range of 1,000 to 40,000. In another embodiment a composition is administered to a patient to suppress appetite, prevent weight gain and/or induce weight loss by the administration of a pharmaceutical composition comprising a glucagon peptide selected from the group consisting of SEQ ID NO: 24, SEQ ID NO: 25, SEQ ID NO: 32, SEQ ID NO: 33, SEQ ID NO: 34 and SEQ ID NO: 35. In one embodiment the glucagon peptide selected from the group consisting of SEQ ID NO: 24, SEQ ID NO: 25, SEQ ID NO: 32, SEQ ID NO: 33, SEQ ID NO: 34 and SEQ ID NO: 35 is further modified to comprise a PEG chain covalently bound to amino acid position 21 or 24. In one embodiment the molecular weight of the PEG chain is selected from the range of 500 to 5,000 Daltons, and in another embodiment the glucagon peptide is selected from the group consisting of SEQ ID NO: 24, SEQ ID NO: 25, SEQ ID NO: 32, SEQ ID NO: 33, SEQ ID NO: 34 and SEQ ID NO: 35 wherein the molecular weight of the PEG chain is selected from the range of 10,000 to 40,000 Daltons.

Exendin-4, is a peptide made up of 39 amino acids. It is a powerful stimulator of a receptor known as GLP-1. This peptide has also been reported to suppress appetite and induce weight loss. Applicants have found that the terminal sequence of Exendin-4 when added at the carboxy terminus of glucagon improves the solubility and stability of glucagon without compromising the bioactivy of glucagon. In one embodiment the terminal ten amino acids of Exendin-4 (i.e. the sequence of SEQ ID NO: 19 (GPSSGAPPPS)) are linked to the carboxy terminus of a glucagon peptide of the present disclosure. These fusion proteins are anticipated to have pharmacological activity for suppressing appetite and inducing weight loss/weight maintenance. In one embodiment the terminal amino acid of the SEQ ID NO: 19 extension comprises an amide group in place of the carboxy group.

In one embodiment a method of reducing weight gain or inducing weight loss in an individual comprises administering an effective amount of a composition comprising a glucagon agonist comprising a glucagon peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18 wherein amino acid 29 of the glucagon peptide is bound to a second peptide through a peptide bond, and said second peptide comprises the sequence of SEQ ID NO: 19 (GPSSGAPPPS). In one embodiment the glucagon peptide of the glucagon agonist is selected from the group consisting of SEQ ID NO: 1, SEQ ID NO: 2, SEQ ID NO: 3, SEQ ID NO: 4, SEQ ID NO: 7, SEQ ID NO: 8, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, wherein the molecular weight of the PEG chain, when present is selected from the range of 500 to 40,000 Daltons. In another embodiment the glucagon peptide portion of the fusion peptide comprises SEQ ID NO: 10, SEQ ID NO: 11, SEQ ID NO: 13, SEQ ID NO: 14, SEQ ID NO: 15, SEQ ID NO: 16, SEQ ID NO: 17 and SEQ ID NO: 18, wherein a PEG chain of about 1,000 to 40,000 Daltons is covalently bound to an amino acid residue at position 21 or 24. In one embodiment the glucagon peptide segment is selected from the group consisting of SEQ ID NO: 7, SEQ ID NO: 8, SEQ ID NO: 10, SEQ ID NO: 11, SEQ ID NO: 17 and SEQ ID NO: 18, wherein the molecular weight of the PEG chain, when present is selected from the range of 500 to 40,000 Daltons. More particularly, in one embodiment the glucagon peptide is selected from the group consisting of SEQ ID NO: 7 and SEQ ID NO: 8 wherein the molecular weight of the PEG chain is selected from the range of 1,000 to 5,000.

In another embodiment a composition is administered to a patient to suppress appetite, prevent weight gain and/or induce weight loss by the administration of a pharmaceutical composition comprising a first pegylated glucagon peptide and a second pegylated glucagon peptide, wherein the first and second peptide are fusion peptides comprising a c-terminal peptide extension comprising SEQ ID NO: 19 (GPSS-GAPPPS). The first pegylated glycogen peptide comprising a covalently linked PEG of about 500 to about 10,000 Daltons and the second pegylated glucagon peptide comprising a covalently linked PEG chain of about 10,000 to about 40,000 Daltons.

In accordance with one embodiment, a glucagon analogue is provided wherein a plasma protein has been covalently linked to an amino acid side chain of the glucagon peptide to improve the solubility, stability and/or pharmacokinetics of the glucagon peptide. For example, serum albumin can be covalently bound to glucagon or a glucagon analogue of the present invention. In one embodiment the plasmid protein is covalently bound to position 16, 17, 20 21, 24 or 29, and more particularly, in one embodiment the plasmid protein is bound at position 21 or 24 of the glucagon peptide. In one embodiment the glucagon peptide is selected from the group consisting of SEQ ID NO: 1, SEQ ID NO: 2, SEQ ID NO: 3, SEQ ID NO: 4, SEQ ID NO: 5, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 24, SEQ ID NO: 25, SEQ ID NO: 32, SEQ ID NO: 33, SEQ ID NO: 34, SEQ ID NO: 35, SEQ ID NO: 37, SEQ ID NO: 38, SEQ ID NO: 39, SEQ ID NO: 40 and SEQ ID NO: 41. In one embodiment the glucagon peptide is selected from the group consisting of SEQ ID NO: 1, SEQ ID NO: 5, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 37, SEQ ID NO: 38, SEQ ID NO: 39, SEQ ID NO: 40 and SEQ ID NO: 41. In one embodiment the glucagon peptide is selected from the group consisting of SEQ ID NO: 1, SEQ ID NO: 5, SEQ ID NO: 15, SEQ ID NO: 16, SEQ ID NO: 17, SEQ ID NO: 18, SEQ ID NO: 37, SEQ ID NO: 38, SEQ ID NO: 39, SEQ ID NO: 40 and SEQ ID NO: 41. In one embodiment the glucagon analog comprises a glucagon peptide selected from the group consisting of SEQ ID NO: 1, SEQ ID NO: 2, SEQ ID NO: 3, and SEQ ID NO: 4, wherein amino acid 29 of the glucagon peptide is bound to a second peptide through a peptide bond, said second peptide comprising the sequence of SEQ ID NO: 19, SEQ ID NO: 20 or SEQ ID NO: 21, and a plasma protein is bound to the side chain of the amino acid located at position 21 or 24.

The present disclosure also encompasses multimers of the modified glucagon peptides disclosed herein. Two or more of the modified glucagon peptides can be linked together using standard linking agents and procedures known to those skilled in the art. For example, dimers can be formed between two modified glucagon peptides through the use of bifunctional thiol crosslinkers and bi-functional amine crosslinkers, particularly for the glucagon peptides that have been substituted with cysteine, lysine ornithine, homocysteine or acetyl phenylalanine residues (e.g. SEQ ID NO: 2 and SEQ ID NO: 3). The dimer can be a homodimer or alternatively can be a heterodimer. In one embodiment the dimer comprises a homodimer of a glucagon fusion peptide wherein the glucagon peptide portion comprises an agonist derivative of SEQ ID NO: 1 and the second peptide comprising an amino acid sequence of SEQ ID NO: 19 (GPSSGAPPPS), SEQ ID NO: 20 (KRNRNNIA) or SEQ ID NO: 21 (KRNR) linked to amino acid 29 of the glucagon peptide. In another embodiment the dimer comprises a homodimer of a glucagon agonist derivative of SEQ ID NO: 1, wherein the glucagon peptide further comprises a polyethylene glycol chain covalently bound to position 21 or 24 of the glucagon peptide.

In accordance with one embodiment a dimer is provided comprising a first glucagon peptide bound to a second glucagon peptide via a linker, wherein said first glucagon peptide is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9 and the second glucagon peptide is independently selected from the group consisting of SEQ ID NO: 5, SEQ ID NO: 6, SEQ ID NO: 7, SEQ ID NO: 8 and SEQ ID NO: 9, and pharmaceutically acceptable salts of said glucagon polypeptides. In one embodiment the first glucagon peptide is selected from the group consisting of SEQ ID NO: 1, SEQ ID NO: 7, SEQ ID NO: 8, SEQ ID NO: 10, SEQ ID NO: 11, SEQ ID NO: 17 and SEQ ID NO: 18 and the second glucagon peptide is independently selected from the group consisting of SEQ ID NO: 7, SEQ ID NO: 8, SEQ ID NO: 10, SEQ ID NO: 11, SEQ ID NO: 17 and SEQ ID NO: 18. In one embodiment the first glucagon peptide is selected from the group consisting of SEQ ID NO: 7 and SEQ ID NO: 8 and the second glucagon peptide is independently selected from the group consisting of SEQ ID NO: 7 and SEQ ID NO: 8.

The modified glucagon peptides of the present invention can be provided in accordance with one embodiment as part of a kit. In one embodiment a kit for administering a glucagon agonist to a patient in need thereof is provided wherein the kit comprises a modified glucagon peptide selected from the group consisting of 1) a pegylated glucagon peptide, wherein the PEG chain is covalently bound to position 16, 17, 20, 21, 24 or 29 of the glucagon peptide, and the PEG chain has a molecular weight of about 500 to about 40,000 Daltons; 2) a glucagon fusion peptide comprising a glucagon agonist derivative of SEQ ID NO: 1, and an amino acid sequence of SEQ ID NO: 19 (GPSSGAPPPS), SEQ ID NO: 20 (KRNRNNIA) or SEQ ID NO: 21 (KRNR) linked to amino acid 29 of the glucagon peptide; and 3) a pegylated glucagon peptide, further comprising an amino acid sequence of SEQ ID NO: 19 (GPSSGAPPPS), SEQ ID NO: 20 (KRNRNNIA) or SEQ ID NO: 21 (KRNR) linked to amino acid 29 of the glucagon peptide, wherein the PEG chain covalently bound to position 16, 17, 20, 21, 24 or 29 has a molecular weight of about 500 to about 40,000 Daltons. In one embodiment the kit is provided with a device for administering the glucagon composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the glucagon composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

EXAMPLES

General Synthesis Protocol

Glucagon analogs were synthesized using HBTU-activated "Fast Boc" single coupling starting from 0.2 mmole of Boc Thr(OBzl)Pam resin on a modified Applied Biosystem 430 A peptide synthesizer. Boc amino acids and HBTU were obtained from Midwest Biotech (Fishers, Ind.). Side chain protecting groups used were: Arg(Tos), Asn(Xan), Asp (OcHex), Cys(pMeBzl), His(Bom), Lys(2Cl—Z), Ser (OBzl), Thr(OBzl), Tyr(2Br—Z), and Trp(CHO). The side-chain protecting group on the N-terminal His was Boc.

Each completed peptidyl resin was treated with a solution of 20% piperidine in dimethylformamide to remove the formyl group from the tryptophan. Liquid hydrogen fluoride cleavages were performed in the presence of p-cresol and dimethyl sulfide. The cleavage was run for 1 hour in an ice bath using an HF apparatus (Penninsula Labs). After evaporation of the HF, the residue was suspended in diethyl ether and the solid materials were filtered. Each peptide was extracted into 30-70 ml aqueous acetic acid and a diluted aliquot was analyzed by HPLC [Beckman System Gold, 0.46×5 cm Zorbax C8, 1 ml/min, 45 C, 214 nm, A buffer=0.1% TFA, B=0.1% TFA/90% acetonitrile, gradient of 10% to 80% B over 10 min].

Purification was done on a FPLC over a 2.2×25 cm Kromasil C18 column while monitoring the UV at 214 nm and collecting 5 minute fractions. The homogeneous fractions were combined and lyophilized to give a product purity of >95%. The correct molecular mass and purity were confirmed using MALDI-mass spectral analysis.

General Pegylation Protocol: (Cys-Maleimido)

Typically, the glucagon Cys analog is dissolved in phosphate buffered saline (5-10 mg/ml) and 0.01M ethylenediamine tetraacetic acid is added (10-15% of total volume). Excess (2-fold) maleimido methoxyPEG reagent (Nektar) is added and the reaction stirred at room temp while monitoring reaction progress by HPLC. After 8-24 hrs, the reaction mixture, is acidified and loaded onto a preparative reverse phase column for purification using 0.1% TFA/acetonitrile gradient. The appropriate fractions were combined and lyophilized to give the desired pegylated derivatives.

Example 1

Synthesis of Glucagon $Cys^{17}$(1-29) and Similar MonoCys Analogs 0.2 mmole Boc Thr(OBzl) Pam resin (SynChem Inc) in a 60 ml reaction vessel and the following sequence was entered and run on a modified Applied Biosystems 430A Peptide Synthesizer using FastBoc HBTU-activated single couplings.

(SEQ ID NO: 28)
HSQGTFTSDYSKYLDSCRAQDFVQWLMNT

The following side chain protecting groups were used: Arg (Tos), Asp(OcHex), Asn(Xan), Cys(pMeBzl), Glu(OcHex), His(Boc), Lys(2Cl—Z), Ser(Bzl), Thr(Bzl), Trp(CHO), and Tyr(Br—Z). The completed peptidyl resin was treated with 20% piperidine/dimethylformamide to remove the Trp formyl protection then transferred to an HF reaction vessel and dried in vacuo. 1.0 ml p-cresol and 0.5 ml dimehyl sulfide were added along with a magnetic stir bar. The vessel was attached to the HF apparatus (Pennisula Labs), cooled in a dry ice/methanol bath, evacuated, and aprox. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] with a small sample of the cleavage extract. The remaining extract was loaded onto a 2.2×25 cm Kromasil C18 preparative reverse phase column and an acetonitrile gradient was run using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min.

The fractions containing the purest product (48-52) were combined frozen, and lyophilized to give 30.1 mg. An HPLC analysis of the product demonstrated a purity of >90% and MALDI mass spectral analysis demonstrated the desired mass of 3429.7. Glucagon $Cys^{21}$, Glucagon $Cys^{24}$, and Glucagon $Cys^{29}$ were similarly prepared.

Example 2

Synthesis of Glucagon-Cex and Other C-Terminal Extended Analogs 285 mg (0.2 mmole) methoxybenzhydrylamine resin (Midwest Biotech) was placed in a 60 ml reaction vessel and the following sequence was entered and run on a modified Applied Biosystems 430A peptide synthesizer using FastBoc HBTU-activated single couplings.

(SEQ ID NO: 29)
HSQGTFTSDYSKYLDSRRAQDFVQWLMNTGPSSGAPPPS

The following side chain protecting groups were used: Arg (Tos), Asp(OcHex), Asn(Xan), Cys(pMeBzl), Glu(OcHex), His(Boc), Lys(2Cl—Z), Ser(Bzl), Thr(Bzl), Trp(CHO), and Tyr(Br—Z). The completed peptidyl resin was treated with 20% piperidine/dimethylformamide to remove the Trp formyl protection then transferred to HF reaction vessel and dried in vacuo. 1.0 ml p-cresol and 0.5 ml dimehyl sulfide were added along with a magnetic stir bar. The vessel was attached to the HF apparatus (Pennisula Labs), cooled in a dry ice/methanol bath, evacuated, and aprox. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] on an aliquot of the cleavage extract. The extract was loaded onto a 2.2×25 cm Kromasil C18 preparative reverse phase column and an acetonitrile gradient was run for elution using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min Fractions 58-65 were combined, frozen and lyophilized to give 198.1 mg.

HPLC analysis of the product showed a purity of greater than 95%. MALDI mass spectral analysis showed the presence of the desired theoretical mass of 4316.7 with the product as a C-terminal amide. Oxyntomodulin and oxyntomodulin-KRNR were similarly prepared as the C-terminal carboxylic acids starting with the appropriately loaded PAM-resin.

Example 3

Glucagon $Cys^{17}$ Mal-PEG-5K 15.1 mg of Glucagon $Cys^{17}$(1-29) and 27.3 mg methoxy poly(ethyleneglycol) maleimide avg. M.W.5000 (mPEG-Mal-5000, Nektar Therapeutics) were dissolved in 3.5 ml phosphate buffered saline (PBS) and 0.5 ml 0.01M ethylenediamine tetraacetic acid (EDTA) was added. The reaction was stirred at room temperature and the progress of the reaction was monitored by HPLC analysis [0.46×5 cm Zorbax C8, 1 ml/min, 45 C, 214 nm (0.5 A), A=0.1% TFA, B=0.1% TFA/90% ACN, gradient=10% B to 80% B over 10 min.].

After 5 hours, the reaction mixture was loaded onto 2.2×25 cm Kromasil C18 preparastive reverse phase column. An acetonitrile gradient was run on a Pharmacia FPLC while monitoring the UV wavelength at 214 nm and collecting 5 min fractions. A=0.1% TFA, B=0.1% TFA/50% acetonitrile, gradient=30% B to 100% B over 450 min. The fractions corresponding to the product were combined, frozen and lyophilized to give 25.9 mg.

This product was analyzed on HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] which showed a purity of aprox. 90%. MALDI (matrix assisted laser desorption ionization) mass spectral analysis showed a broad mass range (typical of PEG derivatives) of 8700 to 9500. This shows an addition to the mass of the starting glucagon peptide (3429) of approximately 5,000 a.m.u.

Example 4

Glucagon Cys²¹ Mal-PEG-5K 21.6 mg of Glucagon $Cys^{21}$(1-29) and 24 mg mPEG-MAL-5000 (Nektar Therapeutics) were dissolved in 3.5 ml phosphate buffered saline (PBS) and 0.5 ml 0.01M ethylene diamine tetraacetic acid (EDTA) was added. The reaction was stirred at room temp. After 2 hrs, another 12.7 mg of mPEG-MAL-5000 was added. After 8 hrs, the reaction mixture was loaded onto a 2.2×25 cm Vydac C18 preparative reverse phase column and an acetonitrile gradient was run on a Pharmacia FPLC at 4 ml/min while collecting 5 min fractions. A=0.1% TFA, B=0.1% TFA/50% ACN. Gradient=20% to 80% B over 450 min.

The fractions corresponding to the appearance of product were combined frozen and lyophilized to give 34 mg. Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a homogeneous product that was different than starting glucagon peptide. MALDI (matrix assisted laser desorption ionization) mass spectral analysis showed a broad mass range (typical of PEG derivatives) of 8700 to 9700. This shows an addition to the mass of the starting glucagon peptide (3470) of approximately 5,000 a.m.u.

Example 5

Glucagon Cys²⁴ Mal-PEG-5K 20.1 mg Glucagon $C^{24}$(1-29) and 39.5 mg mPEG-Mal-5000 (Nektar Therapeutics) were dissolved in 3.5 ml PBS with stirring and 0.5 ml 0.01M EDTA was added. The reaction was stirred at room temp for 7 hrs, then another 40 mg of mPEG-Mal-5000 was added. After approximately 15 hr, the reaction mixture was loaded onto a 2.2×25 cm Vydac C18 preparative reverse phase column and an acetontrile gradient was run using a Pharmacia FPLC. 5 min fractions were collected while monitoring the UV at 214 nm (2.0 A). A buffer=0.1% TFA, B buffer=0.1% TFA/50% ACN, gradient=30% B to 100% B over 450 min. The fractions corresponding to product were combined, frozen and lyophilized to give 45.8 mg. MALDI mass spectral analysis showed a typical PEG broad signal with a maximum at 9175.2 which is approximately 5,000 a.m.u. more than Glucagon $C^{24}$ (3457.8).

Example 6

Glucagon Cys²⁴ Mal-PEG-20K 25.7 mg of Glucagon $Cys^{24}$(1-29) and 40.7 mg mPEG-Mal-20K (Nektar Therapeutics) were dissolved in 3.5 ml PBS with stirring at room temp. and 0.5 ml 0.01M EDTA was added. After 6 hrs, the ratio of starting material to product was aprox. 60:40 as determined by HPLC. Another 25.1 mg of mPEG-Mal-20K was added and the reaction allowed to stir another 16 hrs. The product ratio had not significantly improved, so the reaction mixture was loaded onto a 2.2×25 cm Kromasil C18 preparative reverse phase column and purified on a Pharmacia FPLC using a gradient of 30% B to 100% B over 450 min. A buffer=0.1% TFA, B buffer=0.1% TFA/50% ACN, flow=4 ml/min, and 5 min fractions were collected while monitoring the UV at 214 nm (2.0 A). The fractions containing homogeneous product were combined, frozen and lyophilized to give 25.7 mg. Purity as determined by analytical HPLC was ~90%. A MALDI mass spectral analysis showed a broad peak from 23,000 to 27,000 which is approximately 20,000 a.m.u. more than starting Glucagon $C^{24}$ (3457.8).

Example 7

Glucagon Cys²⁹ Mal-PEG-5K 20.0 mg of Glucagon $Cys^{29}$(1-29) and 24.7 mg mPEG-Mal-5000 (Nektar Therapeutics) were dissolved in 3.5 ml PBS with stirring at room temperature and 0.5 ml 0.01M EDTA was added. After 4 hr, another 15.6 mg of mPEG-Mal-5000 was added to drive the reaction to completion. After 8 hrs, the reaction mixture was loaded onto a 2.2×25 cm Vydac C18 preparative reverse phase column and an acetonitrile gradient was run on a Pharmacia FPLC system. 5 min fractions were collected while monitoring the UV at 214 nm (2.0 A). A=0.1% TFA, B=0.1% TFA/50% ACN. Fractions 75-97 were combined frozen and lyophilized to give 40.0 mg of product that is different than recovered starting material on HPLC (fractions 58-63). Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a purity greater than 95%. MALDI mass spectral analysis showed the presence of a PEG component with a mass range of 8,000 to 10,000 (maximum at 9025.3) which is 5,540 a.m.u. greater than starting material (3484.8).

Example 8

Glucagon Cys²⁴ (2-butyrolactone)

To 24.7 mg of Glucagon $Cys^{24}$(1-29) was added 4 ml 0.05M ammonium bicarbonate/50% acetonitrile and 5.5 ul of a solution of 2-bromo-4-hydroxybutyric acid-γ-lactone (100 ul in 900 ul acetonitrile). After 3 hrs of stirring at room temperature, another 105 ul of lactone solution was added to the reaction mixture which was stirred another 15 hrs. The reaction mixture was diluted to 10 ml with 10% aqueous acetic acid and was loaded onto a 2.2×25 cm Kromasil C18 preparative reverse phase column. An acetonitrile gradient (20% B to 80% B over 450 min) was run on a Pharmacia FPLC while collecting 5 min fractions and monitoring the UV at 214 nm (2.0 A). Flow=4 ml/min, A=0.1% TFA, B=0.1% TFA/50% ACN. Fractions 74-77 were combined frozen and lyophilized to give 7.5 mg. HPLC analysis showed a purity of 95% and MALDI mass spect analysis showed a mass of 3540.7 or 84 mass units more than starting material. This result consistent with the addition of a single butyrolactone moiety.

SEQ ID NO: 30

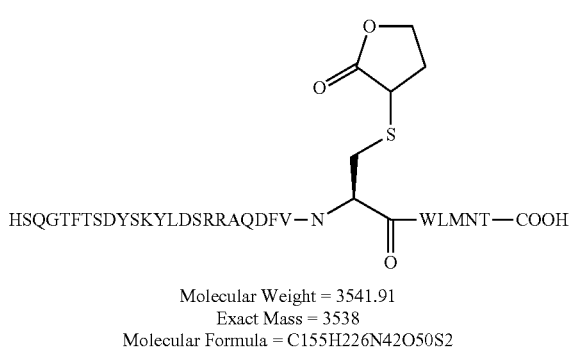

Molecular Weight = 3541.91
Exact Mass = 3538
Molecular Formula = C155H226N42O50S2

Example 9

Glucagon Cys$^{24}$(S-carboxymethyl)

18.1 mg of Glucagon Cys$^{24}$(1-29) was dissolved in 9.4 ml 0.1M sodium phosphate buffer (pH=9.2) and 0.6 ml bromoacetic acid solution (1.3 mg/ml in acetonitrile) was added. The reaction was stirred at room temperature and the reaction progress was followed by analytical HPLC. After 1 hr another 0.1 ml bromoacetic acid solution was added. The reaction was stirred another 60 min then acidified with aqueous acetic acid and was loaded onto a 2.2×25 cm Kromasil C18 preparative reverse phase column for purification. An acetonitrile gradient was run on a Pharmacia FPLC (flow=4 ml/min) while collecting 5 min fractions and monitoring the UV at 214 nm (2.0 A). A=0.1% TFA, B=0.1% TFA/50% ACN. Fractions 26-29 were combined frozen and lyophilized to give several mg of product. Analytical HPLC showed a purity of 90% and MALDI mass spectral analysis confirmed a mass of 3515 for the desired product.

SEQ ID NO: 31

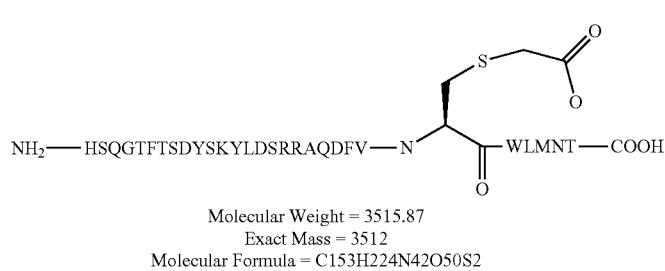

Molecular Weight = 3515.87
Exact Mass = 3512
Molecular Formula = C153H224N42O50S2

Example 10

Glucagon Cys$^{24}$ maleimido,PEG-3.4K-dimer 16 mg Glucagon Cys$^{24}$ and 1.02 mg Mal-PEG-Mal-3400, poly(ethyleneglycol)-bis-maleimide avg. M.W. 3400, (Nektar Therpeutics) were dissolved in 3.5 phosphate buffered saline and 0.5 ml 0.01M EDTA and the reaction was stirred at room temperature. After 16 hrs, another 16 mg of Glucagon Cys$^{24}$ was added and the stirring continued. After approximately 40 hrs, the reaction mixture was loaded onto a Pharmcia PepRPC 16/10 column and an acetonitrile gradient was run on a Pharmacia FPLC while collecting 2 min fractions and monitoring the UV at 214 nm (2.0 A). Flow=2 ml/min, A=0.1% TFA, B=0.1% TFA/50% ACN. Fractions 69-74 were combined frozen and lyophilized to give 10.4 mg. Analytical HPLC showed a purity of 90% and MALDI mass spectral analysis shows a component in the 9500-11,000 range which is consistent with the desired dimer.

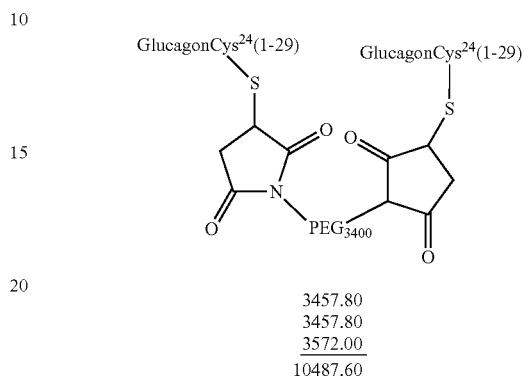

3457.80
3457.80
3572.00
10487.60

Example 11

Glucagon Solubility Assays

A solution (1 mg/ml or 3 mg/ml) of glucagon (or an analog) is prepared in 0.01N HCl. 100 ul of stock solution is diluted to 1 ml with 0.01N HCl and the UV absorbance (276 nm) is determined. The pH of the remaining stock solution is adjusted to pH7 using 200-250 ul 0.1M Na$_2$HPO$_4$ (pH9.2). The solution is allowed to stand overnight at 4° C. then centrifuged. 100 ul of supernatant is then diluted to 1 ml with 0.01N HCl, and the UV absorbance is determined (in duplicate).

The initial absorbance reading is compensated for the increase in volume and the following calculation is used to establish percent solubility:

$$\frac{\text{Final Absorbance}}{\text{Initial Absorbance}} \times 100 = \text{percent soluble}$$

Results are shown in Table 1 wherein Glucagon-Cex represents wild type glucagon (SEQ ID NO: 1) plus a carboxy terminal addition of SEQ ID NO: 19 and Glucagon-Cex R$^{12}$ represents SEQ ID NO: 43 plus a carboxy terminal addition of SEQ ID NO: 19.

TABLE 1

Solubility date for glucagon analogs

| Analog | Percent Soluble |
| --- | --- |
| Glucagon | 16 |
| Glucagon-Cex, R12 | 104 |
| Glucagon-Cex | 87 |
| Oxyntomodulin | 104 |
| Glucagon, Cys17PEG5K | 94 |
| Glucagon, Cys21PEG5K | 105 |
| Glucagon, Cys24PEG5K | 133 |

Example 12

Glucagon Receptor Binding Assay

The affinity of peptides to the glucagon receptor was measured in a competition binding assay utilizing scintillation proximity assay technology. Serial 3-fold dilutions of the peptides made in scintillation proximity assay buffer (0.05 M Tris-HCl, pH 7.5, 0.15 M NaCl, 0.1% w/v bovine serum albumin) were mixed in 96 well white/clear bottom plate (Corning Inc., Acton, Mass.) with 0.05 nM (3-[$^{125}$I]-iodotyrosyl) Tyr10 glucagon (Amersham Biosciences, Piscataway, N.J.), 1-6 micrograms per well, plasma membrane fragments prepared from cells over-expressing human glucagon receptor, and 1 mg/well polyethyleneimine-treated wheat germ agglutinin type A scintillation proximity assay beads (Amersham Biosciences, Piscataway, N.J.). Upon 5 min shaking at 800 rpm on a rotary shaker, the plate was incubated 12 h at room temperature and then read on MicroBeta1450 liquid scintillation counter (Perkin-Elmer, Wellesley, Mass.). Non-specifically bound (NSB) radioactivity was measured in the wells with 4 times greater concentration of "cold" native ligand than the highest concentration in test samples and total bound radioactivity was detected in the wells with no competitor. Percent specific binding was calculated as following: % Specific Binding=((Bound−NSB)/(Total bound−NSB))× 100. $IC_{50}$ values were determined by using Origin software (OriginLab, Northampton, Mass.).

Example 13

Functional Assay—cAMP Synthesis

The ability of glucagon analogs to induce cAMP was measured in a firefly luciferase-based reporter assay. HEK293 cells co-transfected with either glucagon- or GLP-1 receptor and luciferase gene linked to cAMP responsive element were serum deprived by culturing 16 h in DMEM (Invitrogen, Carlsbad, Calif.) supplemented with 0.25% Bovine Growth Serum (HyClone, Logan, Utah) and then incubated with serial dilutions of either glucagon, GLP-1 or novel glucagon analogs for 5 h at 37° C., 5% $CO_2$ in 96 well poly-D-Lysine-coated "Biocoat" plates (BD Biosciences, San Jose, Calif.). At the end of the incubation 100 microliters of LucLite luminescence substrate reagent (Perkin-Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). Effective 50% concentrations were calculated by using Origin software (OriginLab, Northampton, Mass. Results are shown in Tables 2 and 3.

TABLE 2 cAMP Induction by Glucagon Analogs with C-Terminus Extension

| | cAMP Induction | | | |
| --- | --- | --- | --- | --- |
| | Glucagon Receptor | | GLP-1 Receptor | |
| Peptide | $EC_{50}$, nM | N* | $EC_{50}$, nM | N |
| Glucagon | 0.22 ± 0.09 | 14 | 3.85 ± 1.64 | 10 |
| GLP-1 | 2214.00 ± 182.43 | 2 | 0.04 ± 0.01 | 14 |
| Glucagon Cex | 0.25 ± 0.15 | 6 | 2.75 ± 2.03 | 7 |
| Oxyntomodulin | 3.25 ± 1.65 | 5 | 2.53 ± 1.74 | 5 |
| Oxyntomodulin KRNR | 2.77 ± 1.74 | 4 | 3.21 ± 0.49 | 2 |
| Glucagon R12 | 0.41 ± 0.17 | 6 | 0.48 ± 0.11 | 5 |
| Glucagon R12 Cex | 0.35 ± 0.23 | 10 | 1.25 ± 0.63 | 10 |
| Glucagon R12 K20 | 0.84 ± 0.40 | 5 | 0.82 ± 0.49 | 5 |
| Glucagon R12 K24 | 1.00 ± 0.39 | 4 | 1.25 ± 0.97 | 5 |
| Glucagon R12 K29 | 0.81 ± 0.49 | 5 | 0.41 ± 0.24 | 6 |
| Glucagon Amide | 0.26 ± 0.15 | 3 | 1.90 ± 0.35 | 2 |
| Oxyntomodulin C24 | 2.54 ± 0.63 | 2 | 5.27 ± 0.26 | 2 |
| Oxyntomodulin C24 PEG 20K | 0.97 ± 0.04 | 1 | 1.29 ± 0.11 | 1 |

*number of experiments

TABLE 3 cAMP Induction by Pegylated Glucagon Analogs

| | cAMP Induction | | | |
| --- | --- | --- | --- | --- |
| | Glucagon Receptor | | GLP-1 Receptor | |
| Peptide | $EC_{50}$, nM | N* | $EC_{50}$, nM | N |
| Glucagon | 0.33 ± 0.23 | 18 | 12.71 ± 3.74 | 2 |
| Glucagon C17 PEG 5K | 0.82 ± 0.15 | 4 | 55.86 ± 1.13 | 2 |
| Glucagon C21 PEG 5K | 0.37 ± 0.16 | 6 | 11.52 ± 3.68 | 2 |
| Glucagon C24 PEG 5K | 0.22 ± 0.10 | 12 | 13.65 ± 2.95 | 4 |
| Glucagon C29 PEG 5K | 0.96 ± 0.07 | 2 | 12.71 ± 3.74 | 2 |
| Glucagon C24 PEG 20K | 0.08 ± 0.05 | 3 | Not determined | |
| Glucagon C24 Dimer | 0.10 ± 0.05 | 3 | Not determined | |
| GLP-1 | >1000 | | 0.05 ± 0.02 | 4 |

*number of experiments

Example 14

Stability Assay for Glucagon Cys-Maleimido PEG Analogs

Each glucagon analog was dissolved in water or PBS and an initial HPLC analysis was conducted. After adjusting the pH (4, 5, 6, 7), the samples were incubated over a specified time period at 37° C. and re-analyzed by HPLC to determine the integrity of the peptide. The concentration of the specific peptide of interest was determined and the percent remaining intact was calculated relative to the initial analysis. Results for Glucagon $Cys^{21}$-maleimidoPEG$_{5K}$ are shown in FIGS. 1 and 2.

The invention claimed is:

1. A derivative of native glucagon (SEQ ID NO: 1) comprising a hydrophilic moiety covalently bound to the amino acid residue at position 24 of the derivative, wherein the amino acid residue at position 24 is an amino acid selected from the group consisting of lysine, cysteine, ornithine, homocysteine, and acetyl phenylalanine, wherein the derivative stimulates activity at the glucagon receptor, and pharmaceutically acceptable salts of said derivative.

2. The derivative of claim 1 wherein the derivative comprises a sequence selected from the group consisting of SEQ ID NO: 45 and derivatives of SEQ ID NO: 45.

3. The glucagon peptide of claim 2, wherein the peptide comprises a sequence selected from the group consisting of SEQ ID NO: 8, SEQ ID NO: 11, SEQ ID NO: 14, SEQ ID NO: 16, and SEQ ID NO: 18.

4. The derivative of claim 1, wherein said hydrophilic moiety is polyethylene glycol (PEG).

5. The derivative of claim 4, wherein the polyethylene glycol has a molecular weight selected from the range of about 1,000 to about 5,000 Daltons.

6. The derivative of claim 4, wherein the total molecular weight of the PEG is greater than about 5,000 Daltons, optionally, greater than about 10,000 Daltons.

7. The derivative of claim 1 wherein the terminal amino acid of the glucagon peptide comprises an amide group in place of the carboxylic acid group of the native amino acid.

8. A multimer, optionally, a homodimer, comprising two derivatives of claim 1 bound to one another through a linker.

9. A pharmaceutical composition comprising the derivative of claim 1, or pharmaceutically acceptable salt thereof, and a pharmaceutically acceptable carrier.

10. The pharmaceutical composition of claim 9, further comprising insulin.

11. A kit for administering a glucagon agonist to a patient in need thereof, said kit comprising a pharmaceutical composition of claim 9; and a device for administering said composition to a patient.

12. A method of treating hypoglycemia in a patient, said method comprising the steps of administering an effective amount of a pharmaceutical composition of claim 9 to the patient.

13. The derivative of claim 1, wherein the amino acid residue comprising the hydrophilic moiety is cysteine.

14. A derivative of native glucagon (SEQ ID NO: 1) comprising a hydrophilic moiety covalently bound to the amino acid residue at position 24 of the derivative, wherein the derivative comprises SEQ ID NO: 1 with an amino acid substitution at position 12 and/or position 27, optionally, wherein the derivative comprises an Arg at position 12 and/or a Leu or Norleucine at position 27, wherein the derivative stimulates activity at the glucagon receptor, and pharmaceutically acceptable salts of said derivative, optionally, wherein the hydrophilic moiety is polyethylene glycol (PEG).

15. A pharmaceutical composition comprising the glucagon peptide of claim 14, or a pharmaceutically acceptable salt thereof, and a pharmaceutically acceptable carrier.

16. The pharmaceutical composition of claim 15, further comprising insulin.

17. A kit for administering a glucagon agonist to a patient in need thereof, said kit comprising a pharmaceutical composition of claim 15; and a device for administering said composition to a patient.

18. A method of treating hypoglycemia in a patient, said method comprising the steps of administering an effective amount of a pharmaceutical composition of claim 15 to the patient.

19. The glucagon peptide of claim 14, wherein the total molecular weight of the PEG is greater than about 5,000 Daltons, optionally, greater than about 10,000 Daltons.

\* \* \* \* \*

SEQUENCE LISTING

<160> NUMBER OF SEQ ID NOS: 45

<210> SEQ ID NO 1

```
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (21)..(21)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 2

His Ser Gln Gly Thr Phe Thr Ser Asp Tyr Ser Xaa Tyr Leu Asp Ser
1               5                   10                  15

Arg Arg Ala Gln Xaa Phe Val Gln Trp Leu Xaa Asn Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (24)..(24)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 3

His Ser Gln Gly Thr Phe Thr Ser Asp Tyr Ser Xaa Tyr Leu Asp Ser
1               5                   10                  15

Arg Arg Ala Gln Asp Phe Val Xaa Trp Leu Xaa Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
```

```
<222> LOCATION: (12)..(12)
<223> OTHER INFORMATION: Xaa is Lys or Arg
<220> FEATURE:
<221> NAME/KEY: MISC_FEATURE
<222> LOCATION: (21)..(21)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (24)..(24)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 4

His Ser Gln Gly Thr Phe Thr Ser Asp Tyr Ser Xaa Tyr Leu Asp Ser
1               5                   10                  15

Arg Arg Ala Gln Xaa Phe Val Xaa Trp Leu Xaa Asn Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: Glucagon analogue

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (17)..(17)
<223> OTHER INFORMATION: pegylation

<400> SEQUENCE: 6

His Ser Gln Gly Thr Phe Thr Ser Asp Tyr Ser Lys Tyr Leu Asp Ser
1               5                   10                  15

Cys Arg Ala Gln Asp Phe Val Gln Trp Leu Met Asn Thr
            20                  25

<210> SEQ ID NO 7
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (21)..(21)
<223> OTHER INFORMATION: pegylation

<400> SEQUENCE: 7

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Met Asn Thr
```

```
<210> SEQ ID NO 8
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (24)..(24)
<223> OTHER INFORMATION: pegylation

<400> SEQUENCE: 8

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Met Asn Thr
            20                  25

<210> SEQ ID NO 9
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (29)..(29)
<223> OTHER INFORMATION: pegylation

<400> SEQUENCE: 9

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Cys
            20                  25

<210> SEQ ID NO 10
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 10

His Ser Gln Gly Thr Phe Thr Ser Asp Tyr Ser Arg Tyr Leu Asp Ser
1               5                   10                  15

Arg Arg Ala Gln Lys Phe Val Gln Trp Leu Xaa Asn Thr
            20                  25

<210> SEQ ID NO 11
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 11

His Ser Gln Gly Thr Phe Thr Ser Asp Tyr Ser Arg Tyr Leu Asp Ser
1               5                   10                  15
```

```
Arg Arg Ala Gln Asp Phe Val Lys Trp Leu Xaa Asn Thr
            20                  25

<210> SEQ ID NO 12
<211> LENGTH: 29
<212> TYPE: PRT
<213> ORGANISM: Artificial Sequence
<220> FEATURE:
<223> OTHER INFORMATION: Glucagon analogue

<400> SEQUENCE: 12

His Ser Gln Gly Thr Phe Thr Ser Asp Tyr Ser Lys Tyr Leu Asp Ser
1               5                   10                  15

Arg Arg Ala Gln Cys Phe Val Cys Trp Leu Met Asn Thr
            20                  25

<210> SEQ ID NO 13
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 13

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Xaa Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 14

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Xaa Asn Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: Glucagon analogue

<400> SEQUENCE: 15

His Ser Gln Gly Thr Phe Thr Ser Asp Tyr Ser Arg Tyr Leu Asp Ser
1               5                   10                  15

Arg Arg Ala Gln Lys Phe Val Gln Trp Leu Leu Asn Thr
            20                  25

<210> SEQ ID NO 16
<211> LENGTH: 29
<212> TYPE: PRT
```

```
<213> ORGANISM: Artificial Sequence
<220> FEATURE:
<223> OTHER INFORMATION: Glucagon analogue

<400> SEQUENCE: 16

His Ser Gln Gly Thr Phe Thr Ser Asp Tyr Ser Arg Tyr Leu Asp Ser
1               5                   10                  15

Arg Arg Ala Gln Asp Phe Val Lys Trp Leu Leu Asn Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: Glucagon analogue

<400> SEQUENCE: 17

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Leu Asn Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: Glucagon analogue

<400> SEQUENCE: 18

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Leu Asn Thr
            20                  25

<210> SEQ ID NO 19
<211> LENGTH: 10
<212> TYPE: PRT
<213> ORGANISM: Artificial Sequence
<220> FEATURE:
<223> OTHER INFORMATION: peptide fragment representing the carboxy
      terminal 10 amino acids of Exendin-4

<400> SEQUENCE: 19

Gly Pro Ser Ser Gly Ala Pro Pro Pro Ser
1               5                   10

<210> SEQ ID NO 20
<211> LENGTH: 8
<212> TYPE: PRT
<213> ORGANISM: Artificial Sequence
<220> FEATURE:
<223> OTHER INFORMATION: peptide fragment representing the carboxy
      terminal 8 amino acids of oxyntomodulin

<400> SEQUENCE: 20

Lys Arg Asn Arg Asn Asn Ile Ala
1               5

<210> SEQ ID NO 21
<211> LENGTH: 4
<212> TYPE: PRT
<213> ORGANISM: Artificial Sequence
<220> FEATURE:
<223> OTHER INFORMATION: peptide fragment representing the carboxy 4
``` amino acids of oxyntomodulin carboxy terminus

<400> SEQUENCE: 21

Lys Arg Asn Arg
1

<210> SEQ ID NO 22
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 22

His Ser Gln Gly Thr Phe Thr Ser Asp Tyr Ser Lys Tyr Leu Asp Ser
1               5                   10                  15

Arg Arg Ala Gln Cys Phe Val Cys Trp Leu Xaa Asn Thr
            20                  25

<210> SEQ ID NO 23
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (21)..(21)
<223> OTHER INFORMATION: Xaa is Lys or Cys
<220> FEATURE:
<221> NAME/KEY: MISC_FEATURE
<222> LOCATION: (24)..(24)
<223> OTHER INFORMATION: Xaa is Lys or Cys

<400> SEQUENCE: 23

His Ser Gln Gly Thr Phe Thr Ser Asp Tyr Ser Arg Tyr Leu Asp Ser
1               5                   10                  15

Arg Arg Ala Gln Xaa Phe Val Xaa Trp Leu Met Asn Thr
            20                  25

<210> SEQ ID NO 24
<211> LENGTH: 39
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (21)..(21)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 24

His Ser Gln Gly Thr Phe Thr Ser Asp Tyr Ser Xaa Tyr Leu Asp Ser
1               5                   10                  15

Arg Arg Ala Gln Xaa Phe Val Gln Trp Leu Xaa Asn Thr Gly Pro Ser
            20                  25                  30

Ser Gly Ala Pro Pro Pro Ser
        35

<210> SEQ ID NO 25
<211> LENGTH: 37
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (21)..(21)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 25

His Ser Gln Gly Thr Phe Thr Ser Asp Tyr Ser Xaa Tyr Leu Asp Ser
1               5                   10                  15

Arg Arg Ala Gln Xaa Phe Val Gln Trp Leu Xaa Asn Thr Lys Arg Asn
            20                  25                  30

Arg Asn Asn Ile Ala
        35

<210> SEQ ID NO 26
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (21)..(21)
<223> OTHER INFORMATION: Xaa is Lys or Cys

<400> SEQUENCE: 26

His Ser Gln Gly Thr Phe Thr Ser Asp Tyr Ser Lys Tyr Leu Asp Ser
1               5                   10                  15

Arg Arg Ala Gln Xaa Phe Val Gln Trp Leu Met Asn Thr
            20                  25

<210> SEQ ID NO 27
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (24)..(24)
<223> OTHER INFORMATION: Xaa is Lys or Cys

<400> SEQUENCE: 27

His Ser Gln Gly Thr Phe Thr Ser Asp Tyr Ser Lys Tyr Leu Asp Ser
1               5                   10                  15

Arg Arg Ala Gln Asp Phe Val Xaa Trp Leu Met Asn Thr
            20                  25

<210> SEQ ID NO 28
<211> LENGTH: 29

```
<212> TYPE: PRT
<213> ORGANISM: Artificial Sequence
<220> FEATURE:
<223> OTHER INFORMATION: Glucagon analogue

<400> SEQUENCE: 28

His Ser Gln Gly Thr Phe Thr Ser Asp Tyr Ser Lys Tyr Leu Asp Ser
1               5                   10                  15

Cys Arg Ala Gln Asp Phe Val Gln Trp Leu Met Asn Thr
            20                  25

<210> SEQ ID NO 29
<211> LENGTH: 39
<212> TYPE: PRT
<213> ORGANISM: Artificial Sequence
<220> FEATURE:
<223> OTHER INFORMATION: Glucagon Analogue

<400> SEQUENCE: 29

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Ser
            20                  25                  30

Ser Gly Ala Pro Pro Pro Ser
        35

<210> SEQ ID NO 30
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (24)..(24)
<223> OTHER INFORMATION: 2-butyrolactone bound through thiol group of
      cys

<400> SEQUENCE: 30

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Met Asn Thr
            20                  25

<210> SEQ ID NO 31
<211> LENGTH: 29
<212> TYPE: PRT
<213> ORGANISM: Artificial Sequence
<220> FEATURE:
<223> OTHER INFORMATION: Glucagon Analogue
<220> FEATURE:
<221> NAME/KEY: MOD_RES
<222> LOCATION: (24)..(24)
<223> OTHER INFORMATION: carboxymethyl group bound through thiol group
      of cys

<400> SEQUENCE: 31

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Met Asn Thr
            20                  25

<210> SEQ ID NO 32
<211> LENGTH: 39
<212> TYPE: PRT
<213> ORGANISM: Artificial Sequence
```

```
<220> FEATURE:
<223> OTHER INFORMATION: Glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (24)..(24)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 32

His Ser Gln Gly Thr Phe Thr Ser Asp Tyr Ser Xaa Tyr Leu Asp Ser
1               5                   10                  15

Arg Arg Ala Gln Asp Phe Val Xaa Trp Leu Xaa Asn Thr Gly Pro Ser
            20                  25                  30

Ser Gly Ala Pro Pro Ser
        35

<210> SEQ ID NO 33
<211> LENGTH: 37
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (24)..(24)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 33

His Ser Gln Gly Thr Phe Thr Ser Asp Tyr Ser Xaa Tyr Leu Asp Ser
1               5                   10                  15

Arg Arg Ala Gln Asp Phe Val Xaa Trp Leu Xaa Asn Thr Lys Arg Asn
            20                  25                  30

Arg Asn Asn Ile Ala
        35

<210> SEQ ID NO 34
<211> LENGTH: 33
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (21)..(21)
<223> OTHER INFORMATION: Xaa is Lys, Cys, Orn, homocysteine or acetyl
      phenylalanine
```

```
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 34

His Ser Gln Gly Thr Phe Thr Ser Asp Tyr Ser Xaa Tyr Leu Asp Ser
1               5                   10                  15

Arg Arg Ala Gln Xaa Phe Val Gln Trp Leu Xaa Asn Thr Lys Arg Asn
            20                  25                  30

Arg

<210> SEQ ID NO 35
<211> LENGTH: 33
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (24)..(24)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 35

His Ser Gln Gly Thr Phe Thr Ser Asp Tyr Ser Xaa Tyr Leu Asp Ser
1               5                   10                  15

Arg Arg Ala Gln Asp Phe Val Xaa Trp Leu Xaa Asn Thr Lys Arg Asn
            20                  25                  30

Arg

<210> SEQ ID NO 36
<211> LENGTH: 39
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 36

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Xaa Asn Thr Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
```

<223> OTHER INFORMATION: Xaa is Met, Leu or Nle

<400> SEQUENCE: 37

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Xaa Asn Thr Gly Pro Ser
            20                  25                  30

Ser Gly Ala Pro Pro Ser
        35

<210> SEQ ID NO 38
<211> LENGTH: 37
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 38

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Xaa Asn Thr Lys Arg Asn
            20                  25                  30

Arg Asn Asn Ile Ala
        35

<210> SEQ ID NO 39
<211> LENGTH: 37
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 39

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Xaa Asn Thr Lys Arg Asn
            20                  25                  30

Arg Asn Asn Ile Ala
        35

<210> SEQ ID NO 40
<211> LENGTH: 33
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 40

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Xaa Asn Thr Lys Arg Asn
            20                  25                  30

Arg

```
<210> SEQ ID NO 41
<211> LENGTH: 33
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 41
```

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Xaa Asn Thr Lys Arg Asn
            20                  25                  30

Arg

```
<210> SEQ ID NO 42
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (21)..(21)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (24)..(24)
<223> OTHER INFORMATION: Xaa is Lys, Cys, Orn, homocysteine or acetyl
      phenylalanine

<400> SEQUENCE: 42
```

His Ser Gln Gly Thr Phe Thr Ser Asp Tyr Ser Arg Tyr Leu Asp Ser
1               5                   10                  15

Arg Arg Ala Gln Xaa Phe Val Xaa Trp Leu Leu Asn Thr
            20                  25

```
<210> SEQ ID NO 43
<211> LENGTH: 29
<212> TYPE: PRT
<213> ORGANISM: Artificial Sequence
<220> FEATURE:
<223> OTHER INFORMATION: Glucagon analog

<400> SEQUENCE: 43
```

His Ser Gln Gly Thr Phe Thr Ser Asp Tyr Ser Arg Tyr Leu Asp Ser
1               5                   10                  15

Arg Arg Ala Gln Asp Phe Val Gln Trp Leu Met Asn Thr
            20                  25

```
<210> SEQ ID NO 44
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 44
```

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr
            20                  25

<210> SEQ ID NO 45
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (21)..(21)
<223> OTHER INFORMATION: Xaa is Asp, Lys, Cys, Orn, homocysteine or
      acetyl phenylalanine
<220> FEATURE:
<221> NAME/KEY: MISC_FEATURE
<222> LOCATION: (24)..(24)
<223> OTHER INFORMATION: Xaa is Gln, Lys, Cys, Orn, homocysteine or
      acetyl phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 45

His Ser Gln Gly Thr Phe Thr Ser Asp Tyr Ser Xaa Tyr Leu Asp Ser
1               5                   10                  15

Arg Arg Ala Gln Xaa Phe Val Xaa Trp Leu Xaa Asn Thr
            20                  25
```